US011096602B2

(12) United States Patent
Gurevich et al.

(10) Patent No.: US 11,096,602 B2
(45) Date of Patent: Aug. 24, 2021

(54) METHODS AND SYSTEMS FOR CHARACTERIZING TISSUE OF A SUBJECT UTILIZING A MACHINE LEARNING

(71) Applicant: Stryker European Operations Limited, Carrigtwohill (IE)

(72) Inventors: Lina Gurevich, Vancouver (CA); Lori Ann Swalm, Dallas, TX (US)

(73) Assignee: Stryker European Operations Limited, Carrigtwohill (IE)

(*) Notice: Subject to any disclaimer, the term of this patent is extended or adjusted under 35 U.S.C. 154(b) by 477 days.

(21) Appl. No.: 15/663,290

(22) Filed: Jul. 28, 2017

(65) Prior Publication Data
US 2018/0028079 A1    Feb. 1, 2018

Related U.S. Application Data

(60) Provisional application No. 62/368,960, filed on Jul. 29, 2016, provisional application No. 62/368,971, filed on Jul. 29, 2016.

(51) Int. Cl.
*A61B 5/0275* (2006.01)
*G06T 7/557* (2017.01)
(Continued)

(52) U.S. Cl.
CPC .......... *A61B 5/0275* (2013.01); *A61B 5/0261* (2013.01); *A61B 5/7232* (2013.01);
(Continued)

(58) Field of Classification Search
CPC ..... A61B 5/0275; A61B 5/743; A61B 5/7267; A61B 5/7232; A61B 5/0261;
(Continued)

(56) References Cited

U.S. PATENT DOCUMENTS 8,488,863 B2    7/2013   Boucheron
9,892,513 B2    2/2018   Gurevich
(Continued)

FOREIGN PATENT DOCUMENTS

CN       1419428 A      5/2003
CN     101313847 A     12/2008
(Continued)

OTHER PUBLICATIONS

Australian Office Action dated Aug. 7, 2018, for AU Patent Application No. 2016214922, filed on Jul. 27, 2017, two pages.
(Continued)

*Primary Examiner* — Sanjay Cattungal
(74) *Attorney, Agent, or Firm* — Morrison & Foerster LLP

(57) ABSTRACT

Methods and systems for characterizing tissue of a subject include acquiring and receiving data for a plurality of time series of fluorescence images, identifying one or more attributes of the data relevant to a clinical characterization of the tissue, and categorizing the data into clusters based on the attributes such that the data in the same cluster are more similar to each other than the data in different clusters, wherein the clusters characterize the tissue. The methods and systems further include receiving data for a subject time series of fluorescence images, associating a respective cluster with each of a plurality of subregions in the subject time series of fluorescence images, and generating a subject spatial map based on the clusters for the plurality of subregions in the subject time series of fluorescence images. The generated spatial maps may then be used as input for tissue diagnostics using supervised machine learning.

26 Claims, 22 Drawing Sheets
(13 of 22 Drawing Sheet(s) Filed in Color)

(51) Int. Cl.
  *G06K 9/62*   (2006.01)
  *A61B 5/026*  (2006.01)
  *A61B 5/00*   (2006.01)
  *G06K 9/66*   (2006.01)
  *G06T 7/00*   (2017.01)

(52) U.S. Cl.
  CPC ............ *A61B 5/7267* (2013.01); *A61B 5/743* (2013.01); *G06K 9/6218* (2013.01); *G06K 9/6219* (2013.01); *G06K 9/6223* (2013.01); *G06K 9/6274* (2013.01); *G06K 9/66* (2013.01); *G06T 7/0012* (2013.01); *G06T 7/557* (2017.01); *A61B 2576/00* (2013.01); *G06K 2209/05* (2013.01); *G06T 2207/10024* (2013.01); *G06T 2207/10064* (2013.01); *G06T 2207/10081* (2013.01); *G06T 2207/10104* (2013.01); *G06T 2207/30024* (2013.01); *G06T 2207/30104* (2013.01)

(58) Field of Classification Search
  CPC ............ A61B 2576/00; G06K 9/6223; G06K 9/6219; G06K 9/6274; G06K 9/66; G06K 9/6218; G06K 2209/05; G06T 7/557; G06T 7/0012; G06T 2207/10104; G06T 2207/10081; G06T 2207/10024; G06T 2207/30104; G06T 2207/30024; G06T 2207/10064
  See application file for complete search history.

(56) References Cited

U.S. PATENT DOCUMENTS

| | | | |
|---|---|---|---|
| 10,026,159 B2 | 7/2018 | Walle-jensen | |
| 2001/0036304 A1* | 11/2001 | Yang | G06K 9/0014 382/132 |
| 2002/0183621 A1 | 12/2002 | Pfeiffer | |
| 2004/0013292 A1* | 1/2004 | Raunig | G06T 7/0012 382/128 |
| 2005/0043614 A1* | 2/2005 | Huizenga | C23F 11/08 600/427 |
| 2006/0013454 A1* | 1/2006 | Flewelling | A61B 5/7264 382/128 |
| 2006/0247514 A1* | 11/2006 | Panasyuk | A61B 5/0059 600/410 |
| 2007/0016029 A1 | 1/2007 | Donaldson | |
| 2008/0101678 A1 | 5/2008 | Suliga | |
| 2008/0125643 A1 | 5/2008 | Huisman | |
| 2009/0062876 A1* | 3/2009 | Cohen | B82Y 15/00 607/9 |
| 2009/0097723 A1 | 4/2009 | Washburn | |
| 2009/0252682 A1* | 10/2009 | Hillman | A61B 5/418 424/9.1 |
| 2009/0290017 A1 | 11/2009 | Shibasaki | |
| 2010/0215226 A1 | 8/2010 | Kaufman | |
| 2010/0305454 A1 | 12/2010 | Dvorsky et al. | |
| 2011/0071403 A1 | 3/2011 | Sevick-muraca | |
| 2011/0208061 A1 | 8/2011 | Chang | |
| 2011/0311026 A1* | 12/2011 | Lalena | A61B 6/542 378/98.5 |
| 2012/0070044 A1 | 3/2012 | Avinash | |
| 2012/0155735 A1 | 6/2012 | Friedman et al. | |
| 2012/0214180 A1 | 8/2012 | Hess | |
| 2013/0051651 A1 | 2/2013 | Leary | |
| 2013/0096392 A1* | 4/2013 | Adams | A61B 5/441 600/301 |
| 2013/0195329 A1 | 8/2013 | Canda | |
| 2013/0216482 A1* | 8/2013 | Kwon | A61B 5/4255 424/9.6 |
| 2013/0345560 A1 | 12/2013 | Ferguson, Jr. | |
| 2014/0049555 A1 | 2/2014 | Bzdusek | |
| 2015/0004630 A1 | 1/2015 | Lange | |
| 2016/0253800 A1 | 9/2016 | Gurevich | |
| 2016/0290926 A1* | 10/2016 | Notingher | G01J 3/027 |
| 2016/0314585 A1 | 10/2016 | Thomas | |
| 2016/0350913 A1 | 12/2016 | Nagae et al. | |
| 2017/0071509 A1* | 3/2017 | Pandey | A61B 1/00009 |
| 2017/0084012 A1 | 3/2017 | Walle-jensen | |
| 2017/0100037 A1 | 4/2017 | Harmelin | |
| 2018/0158187 A1 | 6/2018 | Gurevich | |

FOREIGN PATENT DOCUMENTS

| | | |
|---|---|---|
| CN | 101460090 A | 6/2009 |
| CN | 102209495 A | 10/2011 |
| CN | 103491874 A | 1/2014 |
| CN | 104155623 A | 11/2014 |
| CN | 104379062 A | 2/2015 |
| JP | 2001-104237 A | 4/2001 |
| JP | 2001-285858 A | 10/2001 |
| JP | 2001-525580 A | 12/2001 |
| JP | 2003-510121 A | 3/2003 |
| JP | 2005-342434 A | 12/2005 |
| JP | 2008/535600 A | 9/2008 |
| JP | 2008/86670 A | 1/2009 |
| JP | 2009-502270 A | 1/2009 |
| JP | 2009-279150 A | 12/2009 |
| JP | 2010/512900 A | 4/2010 |
| JP | 2011-42581 A | 3/2011 |
| JP | 2011-509789 A | 7/2011 |
| JP | 2011-519589 A | 7/2011 |
| JP | 2012-21002 A | 2/2012 |
| JP | 2012-508053 A | 4/2012 |
| JP | 2012-198139 A | 10/2012 |
| JP | 2012-523877 A | 10/2012 |
| JP | 2013-502263 A | 1/2013 |
| JP | 2013-510289 A | 3/2013 |
| JP | 2015-524329 A | 8/2015 |
| KR | 10-2011-0011655 A | 2/2011 |
| WO | 99/28856 A1 | 6/1999 |
| WO | 01/22870 A1 | 4/2001 |
| WO | 2006/123742 A1 | 12/2006 |
| WO | 2009/127972 A1 | 10/2009 |
| WO | 2010/119356 A2 | 10/2010 |
| WO | 2013/146841 A1 | 10/2013 |
| WO | 2013/190391 A1 | 12/2013 |
| WO | 2014/139021 A1 | 9/2014 |
| WO | 2015/001427 A2 | 1/2015 |
| WO | 2015/052710 A1 | 1/2015 |
| WO | 2016/069788 A1 | 5/2016 |
| WO | 2016/087589 A1 | 6/2016 |
| WO | 2016/123705 A1 | 8/2016 |
| WO | 2017/051230 A1 | 3/2017 |
| WO | 2018/018160 A1 | 2/2018 |

OTHER PUBLICATIONS

Canadian Office Action dated May 23, 2019, for CA Application No. 3,021,481, filed on Jul. 28, 2017, four pages.
Canadian Office Action dated Nov. 26, 2018, for CA Application No. 2,975,295, filed on Jul. 28, 2017, three pages.
Canadian Office Action dated Nov. 7, 2019, for CA Application No. 2,975,295, filed on Jul. 28, 2017, five pages.
European Office Action dated Oct. 2, 2018, for EP Application No. 16746031.0, filed on Aug. 22, 2017, nine pages.
European Search Report dated Sep. 12, 2018, for EP Application No. 16746031.0, filed on Aug. 22, 2017, four pages.
Gannot, I. et al. (Nov. 11, 2004). "Fluorescence Imaging of Lesions, Deep Beneath Tissue Surface." 17th Annual Meeting of the IEEE Lasers and Electro-Optics Society, pp. 898-899.
Hui, F. et al. (Nov. 3, 2014), "Quantitative Spatial and Temporal Analysis of Fluorescein Angiography Dynamics in The Eye," Plos One 9(11):e111330, pp. 1-10.
Igari, K. et al. (Oct. 2013). "Quantitative Evaluation of the Outcomes of Revascularization Procedures for Peripheral Arterial Disease Using Indocyanine Green Angiography," European Journal of Vascular and Endovascular Surgery 46(4):460-465.
International Preliminary Report on Patentability dated Apr. 5, 2018, for PCT/IB2016/001214, filed on Jul. 29, 2016, seven pages.

(56) References Cited

OTHER PUBLICATIONS

International Preliminary Report on Patentability dated Aug. 17, 2017, for PCT/CA2016/050092, filed on Feb. 2, 2016, five pages.
International Preliminary Report on Patentability dated Aug. 24, 2017, for PCT/IB2016/00124, filed on Feb. 5, 2016, seven pages.
International Preliminary Report on Patentability dated Feb. 7, 2019, for PCT Application No. PCT/CA2017/050912, filed on Jul. 28, 2017, eight pages.
International Search Report and Written Opinion dated Apr. 22, 2016 for PCT/IB2016/00124, filed on Feb. 5, 2016, eleven pages.
International Search Report and Written Opinion dated May 5, 2016 for PCT/CA2016/050092, filed on Feb. 2, 2016, seven pages.
International Search report and Written Opinion dated Nov. 14, 2017, for PCT Application No. PCT/CA2017/050912, filed on Jul. 28, 2017, thirteen pages.
Invitation to Pay Additional Fees and, where Applicable, Protest Fee dated Oct. 5, 2017, for PCT Application No. PCT/CA2017/050912, filed on Jul. 28, 2017, two pages.
Japanese Notice of Allowance dated Mar. 26, 2019, for JP Application No. 2017-540738, filed on Aug. 1, 2017, six pages.
Japanese Office Action dated Feb. 10, 2020, for JP Application No. 2018-556329 ,filed on Aug. 1, 2017, eight pages.
Japanese Office Action dated Nov. 2, 2018, for JP Application No. 2017-540738 filed on Aug. 1, 2017, four pages.
Korean Notice of Allowance dated Jul. 9, 2019 for KR Application No. 2017-7024707 filed on Sep. 1, 2017, three pages.
Korean Office Action dated Jan. 3, 2019 for KR Application No. 2017-7024707 filed on Sep. 1, 2017, six pages.
Lauer, G. et al. (Jul. 2000). "Expression and Proteolysis of Vascular Endothelial Growth Factor is Increased in Chronic Wounds, "Journal of Investigative Dermatology 115(1):12-18.
Leung, D.W. et al. (Dec. 8, 1989). "Vascular Endothelial Growth Factor is a Secreted Angiogenic Mitogen," Science 246:1306-1309.
U.S. Corrected Notice of Allowance dated May 23, 2018, for U.S. Appl. No. 15/224,342, filed Jul. 29, 2016, two pages.
U.S. Final Office Action dated Jan. 30, 2020, for U.S. Appl. No. 15/855,587, filed Dec. 27, 2017, nine pages.
U.S. Non Final Office Action dated Jul. 26, 2019, for U.S. Appl. No. 15/855,587, filed Dec. 27, 2017, ten pages.
U.S. Non Final Office Action dated Oct. 30, 2017, for U.S. Appl. No. 15/224,342, filed Jul. 29, 2016, sixteen pages.
U.S. Non-Final Office Action dated Aug. 24, 2017, for U.S. Appl. No. 15/013,945, filed Feb. 2, 2016, eight pages.
U.S. Notice of Allowance dated Mar. 15, 2018, for U.S. Appl. No. 15/224,342, filed Jul. 29, 2016, eight pages.
U.S. Notice of Allowance dated Sep. 28, 2017, for U.S. Appl. No. 15/013,945, filed Feb. 2, 2016, eight pages.
Wietecha, M.S. et al. (2013) "Mechanisms of Vessel Regression: Toward an Understanding of the Resolution of Angiogenesis," Current Topics in Microbiology and Immunology 367:3-32.
Alander et al. (Jan. 2012). "A Review of Indocyanine Green Fluorescent Imaging in Surgery," International Journal of Biomedical Imaging, 2(7): 27 pages.
Notice of Acceptance for Patent Application dated Jul. 11, 2019, directed to AU Application No. 2016214922; 3 pages.
Benitez et al. (2014). "Contemporary assessment of foot perfusion in patients with critical limb ischemia," Seminars in Vascular Surgery 27(1): 3-15.
Office Action dated May 27, 2020, directed to CA Application No. 3,021,481; 4 pages.
Office Action dated Jul. 6, 2020, directed to CA Application No. 2,975,295; 6 pages.
First Office Action dated Dec. 26, 2019, directed to CN Application No. 201680020302.2; 43 pages.
Second Office Action dated Jul. 17, 2020, directed to CN Application No. 201680020302.2; 38 pages.
First Office Action dated May 7, 2020, directed to CN Application No. 201680068383.3; 23 pages.
Partial Supplementary European Search Report dated Feb. 25, 2020, directed to EP Application No. 17833161.7; 13 pages.
Extended European Search Report dated Jul. 2, 2020, directed to EP Application No. 17833161.7; 12 pages.
Extended European Search Report dated May 20, 2019, directed to EP Application No. 16848205.7; 9 pages.
De Lorenzi et al. (Apr. 2005). "Evaluation of Skin Perfusion after Nipple-Sparing Mastectomy by Indocyanine Green Dye," Journal of Saitama Medical University 32(2): 45-50.
Dissanaike et al. (Oct. 2014). "Variations in burn perfusion over time as measured by portable ICG fluorescence: A case series," Burns & Trauma 2(4): 201-205.
Decision of Refusal dated Sep. 18, 2020, directed to JP Application No. 2018-556329; 11 pages.
Notice of Reasons for Refusal dated Jun. 7, 2019, directed to JP Application No. 2018-515608; 24 pages.
Decision to Grant a Patent dated Dec. 6, 2019, directed to JP Application No. 2018-515608; 7 pages.
Gurevich et al., U.S. Notice of Allowance and Fee(s) Due dated May 14, 2020, directed to U.S. Appl. No. 15/855,587; 9 pages.
Mingyan et al. (Sep. 2011). Modem Aviation Communication Technology. National Defense Industry Press. pp. 62.
Xuping et al., (Aug. 2012). Acupotomology Imaging Diagnostics. Chinese Press of Traditional Chinese Medicine. pp. 20-21.
Li. (2004). Guidance Materials for National Examination of Employment Certificate for Large-scale Medical Equipment Users (MRI Doctors). China Population Press. pp. 19.
Office Action dated Oct. 12, 2020, directed to EP Application No. 16 746 031.0; 6 pages.

* cited by examiner

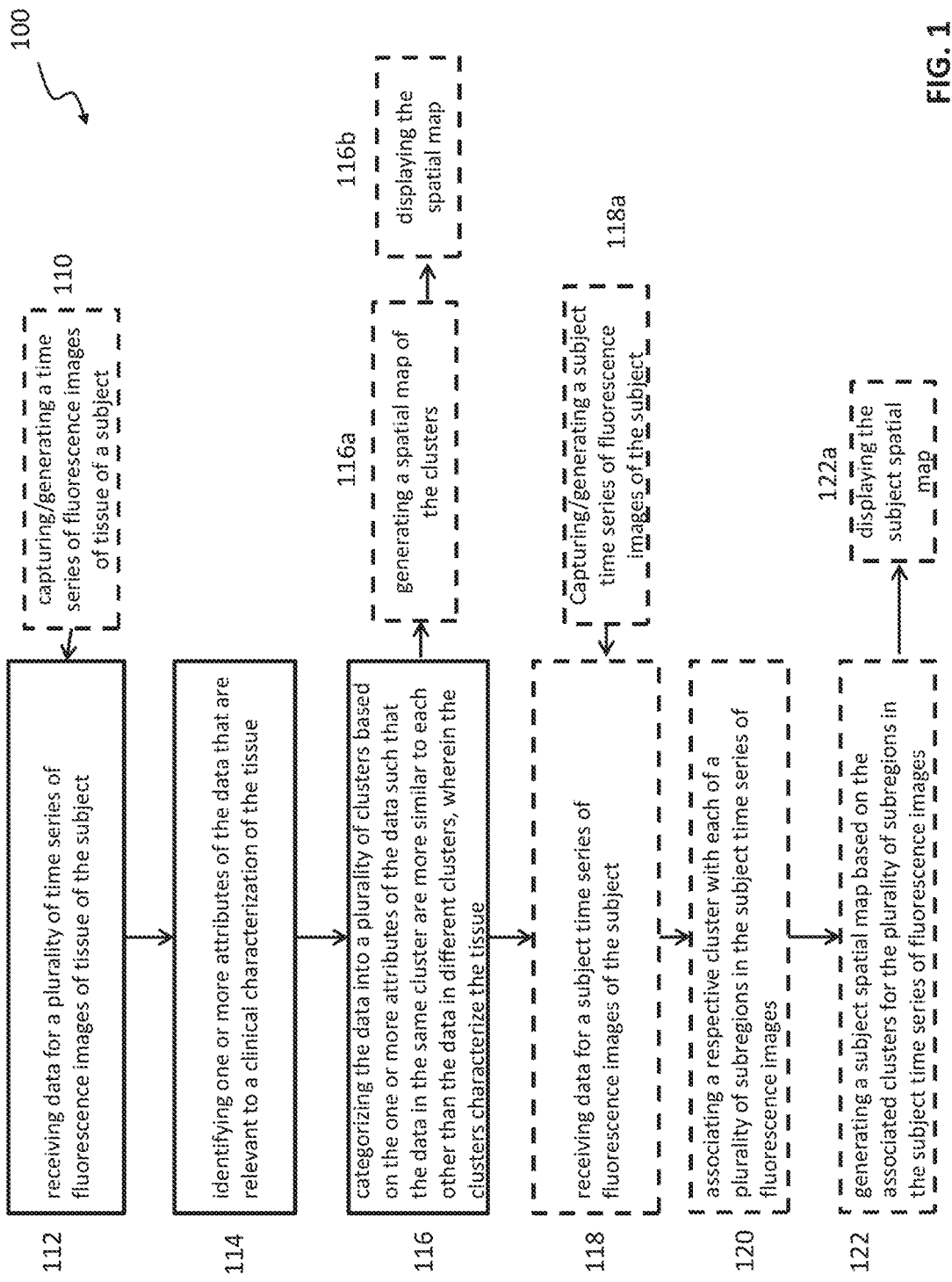

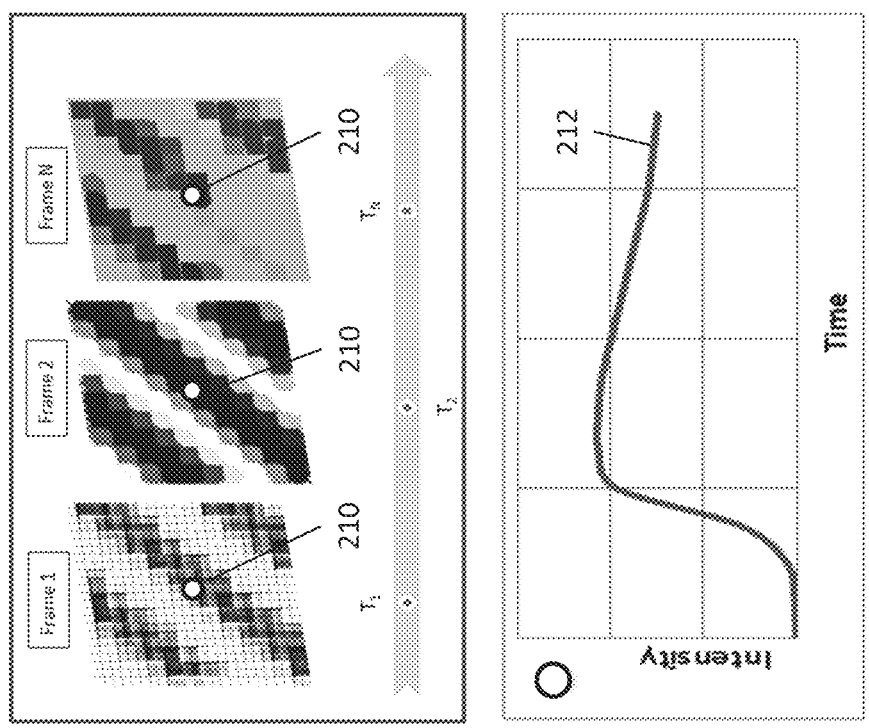

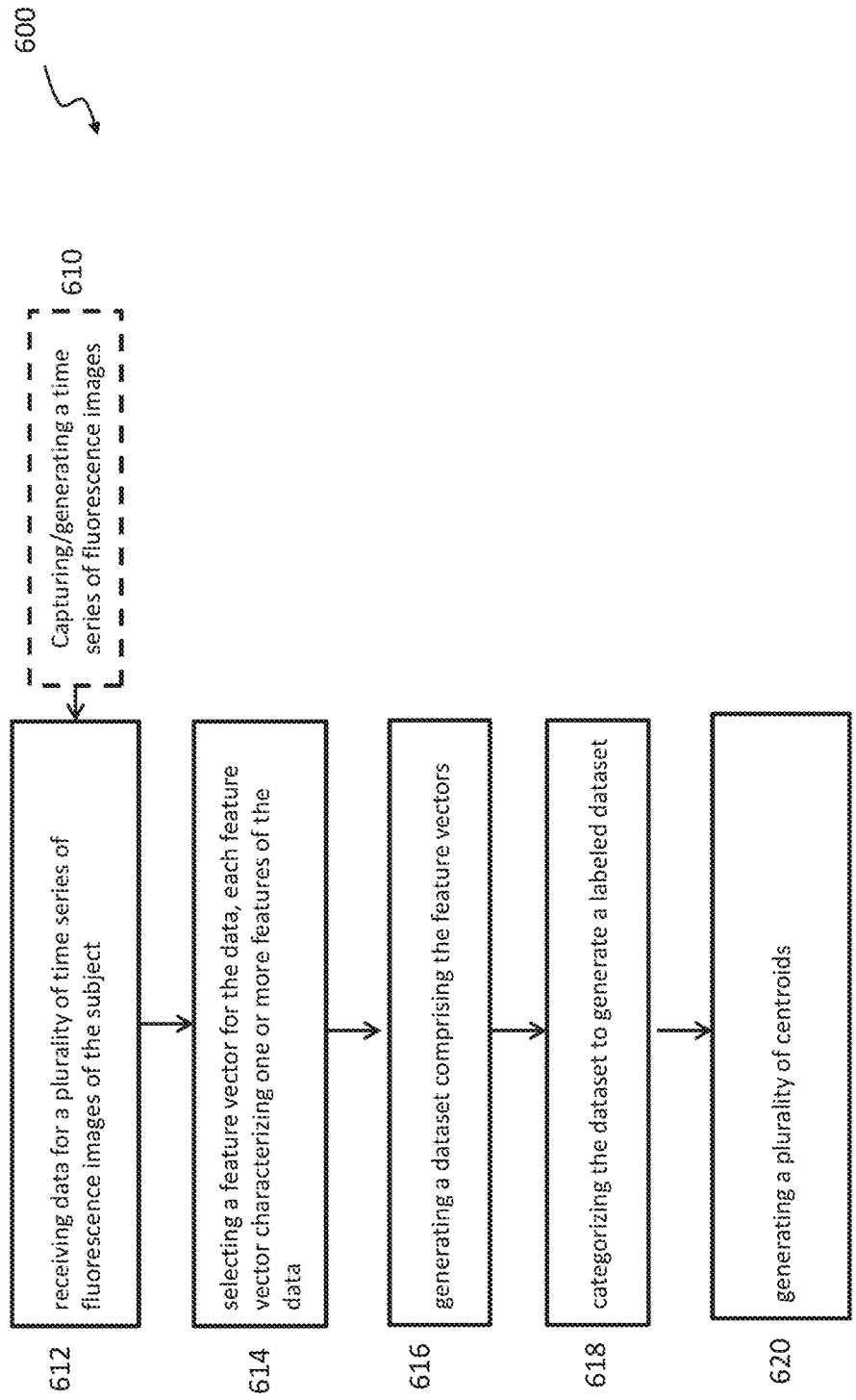

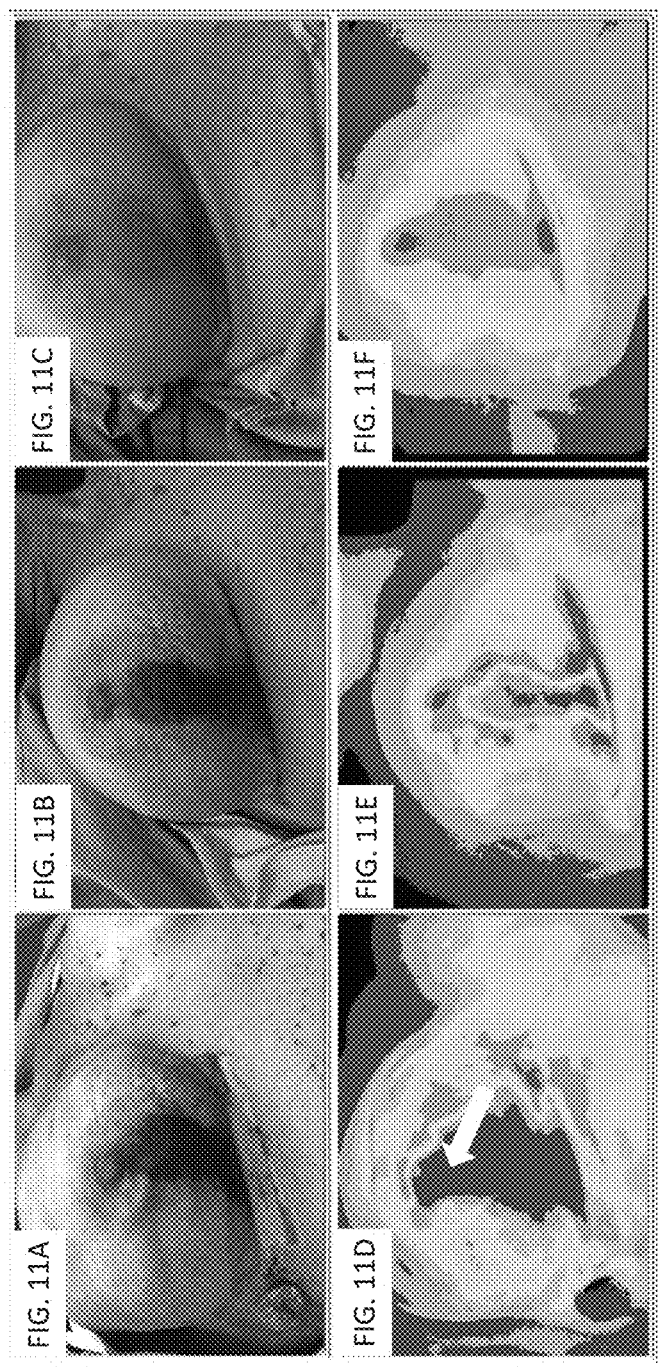

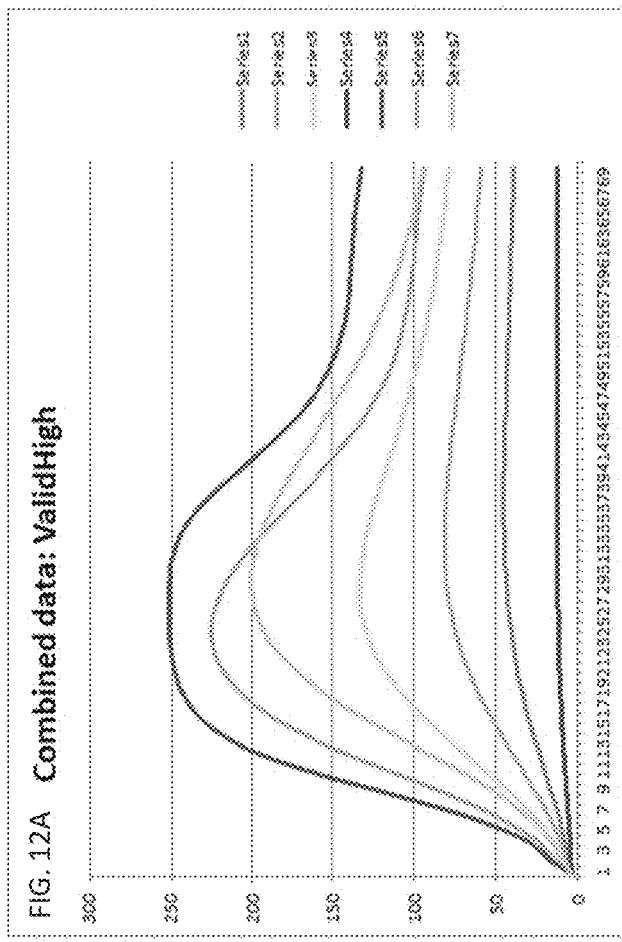
FIG. 12A Combined data: ValidHigh
FIG. 12C
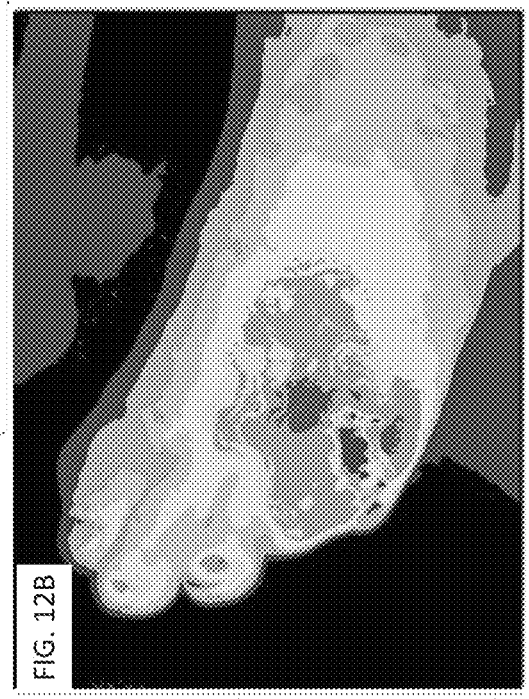
FIG. 12B

METHODS AND SYSTEMS FOR CHARACTERIZING TISSUE OF A SUBJECT UTILIZING A MACHINE LEARNING

REFERENCE TO RELATED APPLICATIONS

This application claims priority to U.S. Provisional Application Ser. Nos. 62/368,960 and 62/368,971, both filed Jul. 29, 2016, and both titled "METHODS AND SYSTEMS FOR CHARACTERIZING TISSUE OF A SUBJECT UTILIZING MACHINE LEARNING," which are hereby incorporated by reference in their entirety.

FIELD OF THE INVENTION

The present invention relates generally to the field of imaging, and more particularly to the acquisition and/or processing of medical images for characterizing tissue of a subject and/or for predicting and displaying clinical data relating to the tissue utilizing machine learning.

BACKGROUND OF THE INVENTION

Blood flow is a generic term used to define movement of blood through blood vessels, which can be quantified in terms such as volumetric flow rate (i.e., volume/time) or travel speed (i.e., distance/time). Tissue perfusion is distinguished from vascular blood flow in that tissue perfusion defines movement of blood through blood vessels within a tissue volume. More specifically, tissue perfusion relates to the microcirculatory flow of blood per unit tissue volume in which oxygen and nutrients are provided to, and waste is removed from, the capillary bed of the tissue being perfused. Perfusion is associated with nutritive blood vessels (i.e., micro-vessels known as capillaries) that comprise the vessels associated with exchange of metabolites between blood and tissue, rather than larger diameter non-nutritive vessels.

There are many circumstances in which medical practitioners desire to correctly assess blood flow and/or tissue perfusion in tissue. For example, in treating patients with wounded tissue, clinicians must correctly assess blood flow and/or tissue perfusion in and around a wound site, since poor tissue perfusion will have an adverse effect on the healing process. An accurate assessment of blood flow and/or tissue perfusion increases the chances of successful healing of both acute (e.g., surgical) and chronic wounds. The assessment of perfusion dynamics is also important in other clinical applications, such as for example pre-surgical evaluation of patients undergoing plastic reconstruction procedures (e.g., skin flap transfers), or assessment of viability and function of cardiac tissue during cardiac surgery (e.g., coronary artery bypass graft surgery).

Certain advanced practices have begun to use imaging technologies such as fluorescence imaging technologies for assessing blood flow and/or tissue perfusion. Fluorescence imaging technologies typically employ the administration of a bolus of an imaging agent (such as for example, indocyanine green (ICG)) that subsequently circulates throughout the subject's tissue, e.g., vasculature and/or lymphatic system, and emits a fluorescence signal when illuminated with the appropriate excitation light. Fluorescence imaging systems acquire images of the emitted imaging agent fluorescence as the imaging agent bolus traverses the subject's tissue in the imaging field of view. For example, the images may be acquired as the bolus enters the tissue through arterial vessels, travels through the tissue's microvasculature, and exits the tissue through the venous vessels. When the images are displayed as video on a monitor, clinicians may observe this imaging agent transit in the vasculature represented as variations in fluorescence intensity with time. Based on their visual perception of the fluorescence intensity, clinicians may make a relative, qualitative determination regarding the blood flow and/or perfusion status of the tissue and its subsequent healing potential. However, a qualitative visual evaluation of such images is not always sufficient for a number of reasons, particularly in instances where the visual information is ambiguous. For instance, such visual evaluation is limited since many parameters, such as image brightness, image contrast and image noise, can be affected by factors other than the blood flow and/or perfusion properties of the tissue. Moreover, mere visual evaluation is subjective (e.g., visual evaluation may vary from clinician to clinician, one clinician's visual evaluation protocol may vary somewhat from patient to patient and/or from imaging session to imaging session) and does not support a standardized protocol for assessing blood flow and/or tissue perfusion. Finally, due to a clinician's lack of memory or inaccurate recollection of previous visual assessments, it can be challenging to reliably and consistently compare and track blood flow and/or perfusion status of a patient over time across multiple imaging sessions.

Several attempts have been made to utilize machine learning algorithms for tissue assessment. Such approaches appear to rely on visual light wound images, and therefore classify wounds based on the wound's surface appearance while disregarding other significant factors (e.g. blood flow patterns) that can be more indicative of the properties and/or status tissue (e.g., tissue health). The methods and systems described herein utilize the advantages of machine learning algorithms in superior pattern recognition in the context of medical imaging of tissue including blood flow dynamics observed in various types of tissue, including wound tissue, and/or lymphatic tissue. As a result, the visual representation of the flow and/or perfusion patterns may be both more accurate and more intuitive than previously demonstrated.

SUMMARY OF THE INVENTION

Described here are variations of methods and systems for characterizing tissue of a subject. Generally, in one variation a method for characterizing tissue of a subject includes receiving data for a plurality of time series of fluorescence images of the subject, identifying one or more attributes of the data that are relevant to a clinical characterization of the tissue, and categorizing the data into a plurality of clusters based on the one or more attributes of the data such that the data in the same cluster are more similar to each other than the data in different clusters, wherein the clusters characterize the tissue.

In some variations, the method may further include receiving data for a subject time series of fluorescence images of the subject, associating a respective cluster with each of a plurality of subregions in the subject time series of fluorescence images, and generating a subject spatial (cluster) map based on the associated clusters for the plurality of subregions in the subject time series of fluorescence images.

The method may further include receiving a plurality of subject spatial maps and receiving metadata associated with each subject spatial map, storing each subject spatial map and its associated clinical data in a record of a database, and using the records of the database as input for a supervised machine learning algorithm for generating a predictive model. The predictive model may be used for predicting clinical data associated with the subject time series of fluorescence images of the subject.

In further variations, a system for characterizing tissue of a subject includes one or more processors and memory having instructions stored thereon, wherein the instructions, when executed by the one or more processors, cause the system to carry out the methods.

According to an aspect is provided a method for characterizing tissue of a subject. The method includes receiving data for a plurality of time series of fluorescence images of the subject, the time series of fluorescence images being or having been captured by an image capture system. The method includes identifying one or more attributes of the data that are relevant to a clinical characterization of the tissue. The method includes categorizing the data into a plurality of clusters based on the one or more attributes of the data such that the data in the same cluster are more similar to each other than the data in different clusters, wherein the clusters characterize the tissue. The method can include generating, based on the categorized clusters, a characterization output representing the tissue.

Optionally, the data for the plurality of time series of fluorescence images of the subject comprises raw data, pre-processed data, or a combination thereof. Optionally, the pre-processed data is pre-processed by applying data compression, principal component analysis, autoencoding, or a combination thereof.

Optionally, the attributes of the data relevant to the clinical characterization of the tissue are identified for a plurality of subregions in the time series of fluorescence images of the subject. Optionally, at least one of the subregions is a pixel or a voxel in the time series of fluorescence images. Optionally, at least one of the subregions is a group of pixels or a group of voxels in the time series of fluorescence images of the subject.

Optionally, the one or more attributes of the data for the plurality of time series of fluorescence images of the subject comprise a time-intensity curve, a coefficient, spatial position, onset time, time to blush, maximum fluorescence intensity, ingress of blood, egress of blood, or a combination thereof.

Optionally, the clusters characterize the tissue based on spatial distribution of the clusters, properties of the clusters, cluster data, or a combination thereof. Optionally, the properties of the clusters comprise shape of the clusters. Optionally, each cluster is represented by a centroid. The centroid may be indicative of which of the one or more attributes of the data for the plurality of time series of fluorescence images of the subject contributes to data categorization.

Optionally, categorizing the data for the plurality of time series of fluorescence images of the subject into the plurality of clusters comprises categorizing the data into ten or fewer clusters. Optionally, categorizing the data for the plurality of time series of fluorescence images of the subject into the plurality of clusters comprises categorizing the data into seven clusters.

Optionally, categorizing the data for the plurality of time series of fluorescence images of the subject comprises applying an unsupervised clustering algorithm. The clustering algorithm may be a K-means algorithm.

Optionally, the method includes generating a spatial map based on the plurality of clusters. The spatial map may represent differences in blood flow, perfusion patterns, or a combination thereof among a plurality of subregions in the time series of fluorescence images.

Optionally, the method includes training a machine learning model based on the categorized data. The machine learning model may be trained in a supervised machine learning algorithm.

Optionally, the method includes having received data for a subject time series of fluorescence images of the subject, associating a respective cluster with each of a plurality of subregions in the subject time series of fluorescence images; and generating a subject spatial map based on the associated clusters for the plurality of subregions in the subject time series of fluorescence images; and optionally displaying the spatial map. The generating the subject spatial map may comprise assigning at least one of an intensity value and a color to each subregion in the subject time series of fluorescence images, based on the associated cluster.

According to an aspect is provided a method of predicting clinical data for tissue of a subject. The method includes receiving a plurality of subject spatial maps generated as described hereinabove and receiving metadata associated with each subject spatial map. The method includes storing each subject spatial map and its associated clinical data in a record of a database. The method includes using the records of the database as input for a supervised machine learning algorithm for generating a predictive model characterizing the tissue.

Optionally, the metadata comprises clinical data, non-clinical data, or a combination thereof. The clinical data may comprise a diagnosis of a tissue abnormality, predicted healing time in a wound, suggested treatment plan, or combination thereof.

According to an aspect is provided a method of predicting clinical data to characterize tissue of a subject. The method includes receiving data for a subject time series of fluorescence images of the subject, the subject time series of fluorescence images of the subject being or having been acquired by an image acquisition device. The method includes using the generated predictive model, for predicting clinical data associated with the subject time series of fluorescence images of the subject to characterize tissue of the subject. The method may include generating a characterization output representing the tissue.

According to an aspect use of a database is provided, for predicting clinical data associated with the subject time series of fluorescence images of the subject.

According to an aspect is provided a method for characterizing tissue of a subject. The method includes receiving data for a subject time series of fluorescence images of the subject, the subject time series of fluorescence images of the subject being or having been acquired by an image acquisition device. The method includes associating a respective category with each of a plurality of subregions in the subject time series of fluorescence images, wherein the categories characterize the tissue and are defined based on one or more attributes relevant to a clinical characterization of the tissue, such that data in the same category are more similar to each other than the data in different categories. The method includes generating a spatial map representing the tissue based on the associated categories for the plurality of subregions in the subject time series of fluorescence images. The method may include displaying the spatial map.

According to an aspect is provided a method for characterizing tissue of a subject. The method includes receiving data for a plurality of time series of fluorescence images, the plurality of time series of fluorescence images being or having been acquired by an image acquisition system. The method includes selecting a feature vector for the data, each feature vector characterizing one or more features of the data. The method includes generating a dataset comprising the feature vectors. The method includes categorizing the dataset to generate a labeled dataset. The method includes generating a plurality of centroids representing a characterization of the tissue. The method may include displaying a characterization output of the tissue based on the plurality of centroids.

According to an aspect is provided a method for characterizing tissue of a subject. The method includes receiving a training dataset comprising a plurality of feature vectors characterizing one or more features of a plurality of data entries, wherein each data entry is at least a portion of a time-intensity curve for a training subregion in a training time series of fluorescence images, the time series of fluorescence images being or having been acquired by an image acquisition system.

According to an aspect is provided a system including one or more processors arranged for causing the system to carry out one or more of the methods. The system may include an image acquisition device arranged for acquiring a time series of fluorescence images.

Optionally, the system includes a display to display a spatial map image, a subject spatial map image or both.

Optionally, the one or more processors is further arranged for superimposing the spatial map image, the subject map image or both on an anatomical image of the tissue.

Optionally, the system includes a light source that provides an excitation light to induce fluorescence emission from a fluorescence imaging agent in the tissue.

Optionally, the system includes an image acquisition assembly that generates the time series of fluorescence images, the subject time series of fluorescence image or both based on the fluorescence emission.

According to an aspect is provided a system for processing a time series of images of tissue of a subject. The system includes a user interface. The system includes a processor arranged for communicating with the user interface. The system includes a non-transitory computer-readable storage medium having instructions stored which, when executed by the processor, cause the processor to perform any one of the methods. The processor may be in communication with an imaging system. The system may include an imaging system. The processor may be a component of the imaging system. The processor may be arranged for controlling an operation of the imaging system.

Optionally, the imaging system is a fluorescence imaging system and the time series of images may be a time series of fluorescence images. The fluorescence imaging system may include an illumination module arranged for illuminating the tissue of the subject to induce fluorescence emission from a fluorescence imaging agent in the tissue of the subject. The fluorescence imaging system may include a camera assembly arranged for acquiring the time series of fluorescence images.

According to an aspect is provided a non-transitory tangible computer-readable medium having computer-executable program code means embedded thereon to perform any one of the methods.

According to an aspect is provided a kit for processing a time series of fluorescence images of tissue of a subject, the kit including the system and a fluorescence imaging agent.

According to an aspect is provided a fluorescence imaging agent for use in the methods or systems. A fluorescence imaging agent can be used in the methods or the systems for wound management. The wound management may include chronic wound management.

Optionally, the fluorescence imaging agent includes Indocyanine Green, ICG. The fluorescence imaging agent may be ICG.

According to an aspect is provided a method for visualizing angiographic data. The method includes the steps of: a) receiving at least one temporal image sequence, the time series of fluorescence images being or having been acquired by an image acquisition system; b) dividing the at least one temporal image sequence into a plurality of temporal sequences of spatial regions of the image of the temporal image sequence; c) automatically dividing the plurality of temporal sequences of spatial regions into a number of clusters, such that the sequences in the same cluster are more similar to each other than sequences from different clusters; d) receiving an angiographic image sequence to be visualized; e) for each pixel in the angiographic image sequence determining with which cluster the temporal sequence of said pixel corresponds; and f) creating an image wherein to each pixel a pixel value is assigned according to the cluster with which said pixel position in the angiographic image sequence has been determined to correspond.

Optionally, the step b) includes determining for each temporal sequence of a spatial region a feature vector representative of a temporal image change in said spatial region.

The feature vector may be determined using a dimensionality reduction machine learning algorithm. The dimensionality reduction machine learning algorithm may be based on principal component analysis, an autoencoder neural network, or a combination thereof.

Optionally, in step b) the temporal sequences of spatial regions are temporal sequences of individual pixels of the image of the temporal image sequence.

Optionally, the step c) is performed using an unsupervised clustering algorithm. The unsupervised clustering algorithm may include a K-means algorithm.

Optionally, the step c) includes automatically dividing the plurality of temporal sequences of spatial regions into a number of clusters using an unsupervised clustering algorithm; dividing the plurality of temporal sequences of spatial regions into a training dataset and a testing dataset; using the training dataset as input for a supervised machine learning algorithm for generating a predictive model; and testing the predictive model on the testing dataset; wherein the step e) includes using the predictive model for determining with which cluster the temporal sequence of said pixel corresponds.

Optionally, the step c) includes automatically dividing the plurality of temporal sequences of spatial regions into a number of clusters on the basis of a time dependence of an intensity of the spatial regions.

Optionally, the step c) includes determining the number of clusters on the basis of cumulative classification error.

According to an aspect is provided a method for visualizing angiographic data, including the steps of: a) retrieving a plurality of masks representative of different time dependencies of an intensity of a spatial region of an image; b) receiving an angiographic image sequence to be visualized; c) for each pixel in the angiographic image sequence determining with which mask the temporal sequence of said pixel corresponds best; and d) creating an image wherein to each pixel a pixel value is assigned according to the mask with which said pixel position in the angiographic image sequence has been determined to correspond.

Optionally, the plurality of masks has been obtained by: e) receiving at least one temporal image sequence; f) dividing the at least one temporal image sequence into a plurality of temporal sequences of spatial regions of the image of the temporal image sequence; g) automatically dividing the plurality of temporal sequences of spatial regions into a number of clusters, such that the sequences in the same cluster are more similar to each other than sequences from different clusters; and h) for each cluster generating a mask representative of the time dependency of the intensity of a spatial region of that cluster. Each mask may be representative of the time dependency of the intensity of a centroid of the respective cluster.

According to an aspect is provided a method of predicting clinical data, including the steps of: a) receiving a plurality of generated angiographic image visualisations; b) for each angiographic image visualisation storing data representative thereof in a record of a database; c) for each angiographic image visualisation storing clinical data associated therewith in the respective record of the database; d) using the records of the database as input for a supervised machine learning algorithm for generating a predictive model; e) receiving an angiographic image sequence to be analyzed; f) visualizing the angiographic image sequence; and g) using the predictive model for predicting clinical data associated with the angiographic image sequence.

According to an aspect is provided a method of predicting clinical data, including the steps of: a) receiving an angiographic image sequence to be analyzed, the time series of fluorescence images being or having been acquired by an image acquisition system; b) visualizing the angiographic image sequence; and c) using a predictive model for predicting clinical data associated with the angiographic image sequence. The predictive model may have been obtained by: d) receiving a plurality of generated angiographic image visualisations; e) for each angiographic image visualisation storing data representative thereof in a record of a database; f) for each angiographic image visualisation storing clinical data associated therewith in the respective record of the database; and g) using the records of the database as input for a supervised machine learning algorithm for generating the predictive model.

According to an aspect is provided use of a database for predicting clinical data associated with the angiographic image sequence.

According to an aspect is provided use of a predictive model for predicting clinical data associated with the angiographic image sequence.

According to an aspect is provided A method for creating a plurality of masks, including the steps of: a) receiving at least one temporal image sequence, the temporal image sequence being or having been acquired by an image acquisition system; b) dividing the at least one temporal image sequence into a plurality of temporal sequences of spatial regions of the image of the temporal image sequence; c) automatically dividing the plurality of temporal sequences of spatial regions into a number of clusters, such that the sequences in the same cluster are more similar to each other than sequences from different clusters; and d) for each cluster generating a mask representative of the time dependency of the intensity of a spatial region of that cluster. Each mask may be representative of the time dependency of the intensity of a centroid of the respective cluster.

According to an aspect is provided use of a plurality of masks obtained by the method, for visualizing angiographic data.

According to an aspect is provided a system for visualizing angiographic data. The system includes a) a first receiving unit for receiving at least one temporal image sequence, the temporal image sequence being or having been acquired by an image acquisition system; b) a dividing unit arranged for dividing the at least one temporal image sequence into a plurality of temporal sequences of spatial regions of the image of the temporal image sequence; c) a clustering unit arranged for automatically dividing the plurality of temporal sequences of spatial regions into a number of clusters, such that the sequences in the same cluster are more similar to each other than sequences from different clusters; d) a second receiving unit for receiving an angiographic image sequence to be visualized; e) a determination unit arranged for each pixel in the angiographic image sequence determining with which cluster the temporal sequence of said pixel corresponds; and f) an image creation unit arranged for creating an image wherein to each pixel a pixel value is assigned according to the cluster with which said pixel position in the angiographic image sequence has been determined to correspond.

According to an aspect is provided a system for visualizing angiographic data. The system includes a) a retrieving unit for retrieving a plurality of masks representative of different time dependencies of an intensity of a spatial region of an image; b) a receiving unit for receiving an angiographic image sequence to be visualized; c) a determination unit arranged for each pixel in the angiographic image sequence determining with which mask the temporal sequence of said pixel corresponds best; and d) an image creation unit arranged for creating an image wherein to each pixel a pixel value is assigned according to the mask with which said pixel position in the angiographic image sequence has been determined to correspond.

According to an aspect is provided a system for creating a plurality of masks. The system includes a) a receiving unit for receiving at least one temporal image sequence, the temporal image sequence being or having been acquired by an image acquisition system; b) a dividing unit arranged for dividing the at least one temporal image sequence into a plurality of temporal sequences of spatial regions of the image of the temporal image sequence; c) a clustering unit arranged for automatically dividing the plurality of temporal sequences of spatial regions into a number of clusters, such that the sequences in the same cluster are more similar to each other than sequences from different clusters; and d) a generation unit arranged for each cluster generating a mask representative of the time dependency of the intensity of a spatial region of that cluster.

It will be appreciated that the methods may be computer implemented methods.

The methods and systems facilitate acquiring and generating visual representations of tissue of a subject that may be more accurate in terms of data representation, and intuitive for clinicians to use for their clinical decision making. The methods and systems, and the visual representations of tissue generated may be applicable to various types of tissue (e.g. a variety of wounds including chronic, acute, pressure ulcers), and may provide a framework for automatically classifying the tissue (e.g., wound tissue) and/or predicting clinical outcomes (e.g., healing timeline for wound tissue).

The methods, systems and kits may be used for blood flow imaging, tissue perfusion imaging, lymphatic imaging, or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the peri-wound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

It will be appreciated that any options mentioned in view of any of the methods may be used in conjunction with the other methods, systems, and kits, and vice versa. It will be appreciated that any of the options may be combined. It will be appreciated that any of the aspects may be combined. Hereinbelow, embodiments and variations thereon are described. It will be appreciated that any of the embodiments and/or variations may be combined with the methods, systems and kits described hereinabove.

BRIEF DESCRIPTION OF THE DRAWINGS

The patent or application file contains at least one drawing executed in color. Copies of this patent or patent application publication with color drawings(s) will be provided by the Office upon request and payment of the necessary fee. Features will become apparent to those of ordinary skill in the art by describing in detail exemplary embodiments with reference to the attached drawings in which:

FIG. 1 is an illustrative block diagram of an exemplary method for characterizing tissue of a subject in a variation;

FIG. 2A is an illustrative depiction of a time series or a subject time series of images. FIG. 2B is an illustrative depiction of a time-intensity curve generated for a subregion in the time series or a subject time series of images;

FIG. 6 is an illustrative block diagram of an exemplary method for characterizing tissue of a subject and/or predicting clinical data;

FIGS. 11A to 11F illustrate application of the methods and systems to breast tissue in reconstructive surgery;

FIG. 12A illustrates the centroids generated for the subject's foot, and FIGS. 12B and 12C illustrate application of the methods and systems described herein to the foot tissue;

DETAILED DESCRIPTION OF THE INVENTION

Figure 3A:
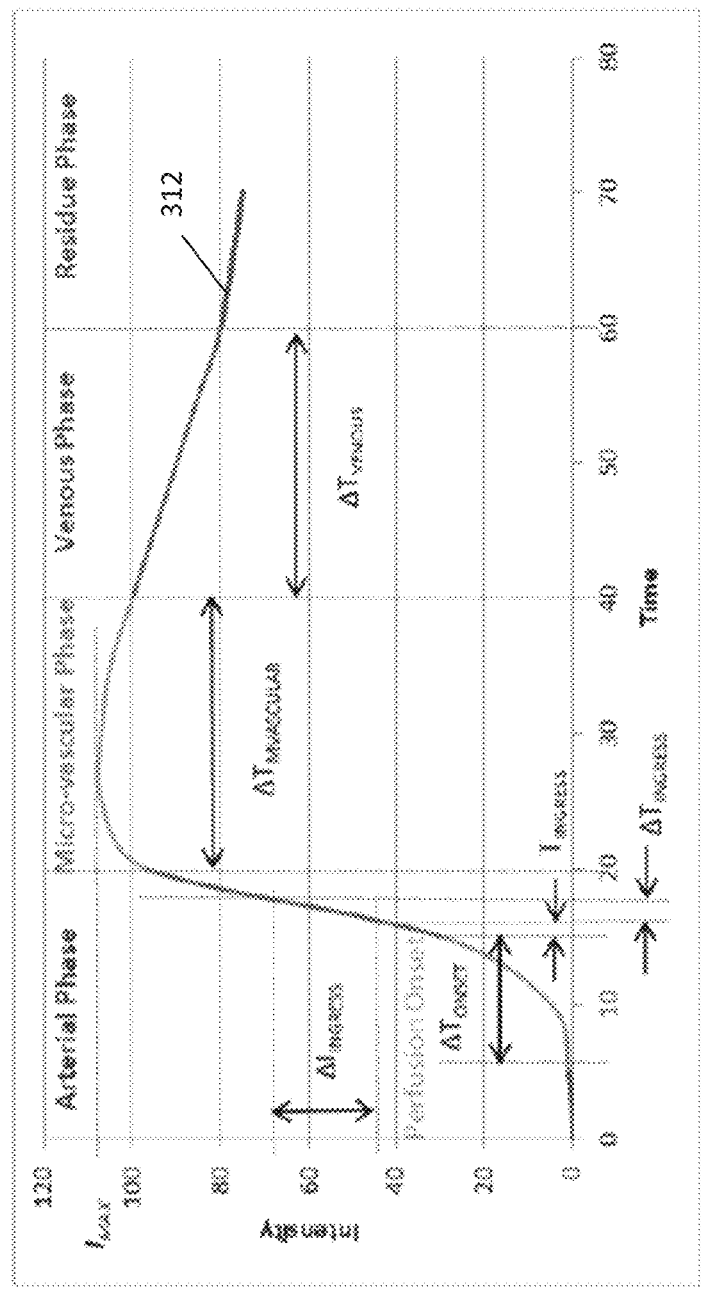
FIG. 3A is an exemplary time-intensity curve with a plurality of exemplary parameters that approximate or otherwise characterize the time-intensity curve.

Reference will now be made in detail to implementations and embodiments of various aspects and variations of the invention, examples of which are illustrated in the accompanying drawings. Various fluorescence imaging and/or processing systems and methods are described herein. Although at least two variations of imaging and/or processing systems and methods are described, other variations of fluorescence imaging and/or processing systems and methods may include aspects of the systems and methods described herein combined in any suitable manner having combinations of all or some of the aspects described. Example embodiments will now be described more fully hereinafter with reference to the accompanying drawings; however, they may be embodied in different forms and should not be construed as limited to the embodiments set forth herein. Rather, these embodiments are provided so that this disclosure will be thorough and complete, and will fully convey exemplary implementations to those skilled in the art. Various devices, systems, methods, processors, kits and imaging agents are described herein. Although at least two variations of the devices, systems, methods, processors, kits and imaging agents are described, other variations may include aspects of the devices, systems, methods, processors, kits and imaging agents described herein combined in any suitable manner having combinations of all or some of the aspects described.

Generally, corresponding or similar reference numbers will be used, when possible, throughout the drawings to refer to the same or corresponding parts.

Spatially relative terms, such as "beneath", "below", "lower", "above", "upper", and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (rotated 90 degrees or at other orientations) and the spatially relative descriptors used herein interpreted accordingly.

The methods and systems described herein facilitate acquiring and generating visual representations of tissue of a subject that may be more accurate in terms of data representation, and intuitive for clinicians to use for their clinical decision making. The methods and systems described herein, and the visual representations of tissue generated may be applicable to various types of tissue (e.g. a variety of wounds including chronic, acute, pressure ulcers), and may provide a framework for automatically classifying the tissue (e.g., wound tissue) and/or predicting clinical outcomes (e.g., healing timeline for wound tissue).

The methods and systems described herein utilize in part machine learning or deep learning. Machine learning-based methods and systems facilitate solving problems that either do not have an algorithmic solution or a solution is too complex to find. Medical diagnosis and tissue characterization based on imaging of the tissue is a task particularly well suited for machine learning algorithms due to complex nature of physiological processes taking place in the human body. Machine learning can be used to discover medically-relevant features and patterns within large datasets and help clinicians make medical diagnoses more accurately, more quickly and more consistently irrespective of the clinician's experience.

The accuracy of a trained predictive model is dependent on the amount and quality of its input data. As a result, the majority of conventionally proposed automatic wound classification frameworks rely on large databases of wound images where a sample input is the image. Classic supervised machine learning methods rely on millions of labeled data samples for training data generation. This presents an issue with regard to medical imaging data such as, for example, fluorescence imaging data because such data must be vast and labeled in order to be used in the classic supervised machine learning.

Furthermore, the quality of the data and the amount of useful information that it contains are key factors that determine how well a classic machine learning model or algorithm can learn. Several challenges arise with using such a model in connection with imaging data such as, for example, fluorescence imaging data, including coping with missing values in the datasets and selecting relevant features for the model construction. Further challenges may arise in connection with learning algorithms and optimization. For example, if a model does not perform well on a test dataset, one has to be able to establish the causes of failure and adjust the model accordingly which can be challenging with medical imaging data. The methods and systems described herein work around the 'big data need' of current machine learning models by utilizing the temporal dimension of pixels intensities, thus allowing construction of training sets from just a handful of patient's sequences.

In addition, by applying clustering machine learning algorithms in various embodiments of the methods and systems of the present invention, the training datasets can be categorized automatically, without involvement of a clinical specialist.

Methods for Characterizing Tissue of a Subject Utilizing Machine Learning

As shown in FIG. 1, an example of a method 100 for characterizing tissue of a subject may include: receiving data for a plurality of time series of fluorescence images of tissue of a subject 112, the plurality of time series of fluorescence images being or having been captured/acquired using an image capture/acquisition device or system, identifying one or more attributes of the data that are relevant to a clinical characterization of the tissue 114 (e.g., various characteristics of the angiographic curve including raw intensity values over time, maximum intensity, ingress rate, egress rate, perfusion onset time, duration of arterial/microvascular/venous phases as described in the specification), categorizing the data into a plurality of clusters based on the one or more attributes of the data such that the data in the same cluster are more similar to each other than the data in different clusters, wherein the clusters characterize the tissue 116, and generating (based on the categorized clusters) a characterization output of the tissue. In some variations a feature vector in connection with the identifying step may be for every pixel and may further include a combination of similar features from neighboring pixels. The identifying step may be manual (e.g., using intensity vs time values), automatic (algorithm-aided, e.g., via principal component analysis as described in the specification), or a combination thereof. In further variations, the method may further comprise receiving data for a subject time series of fluorescence images of the subject 118 (e.g., data acquired/derived from a patient undergoing or having undergone imaging for whom a diagnosis and/or evaluation is sought), associating a respective cluster with each of a plurality of subregions in the subject time series of fluorescence images of the tissue 120, and generating a subject spatial map of the tissue based on the associated clusters for the plurality of subregions in the subject time series of fluorescence images 122. In some variations, the method may yet further comprise displaying the subject spatial map (e.g., an image) 122a. Throughout the specification, "spatial map" and/or "subject spatial map" is used interchangeably with "cluster map" and/or "subject cluster map". Throughout the specification, "subject" includes human subjects and animal subjects (e.g., mammals).

In some variations, at least a portion of the method may be performed by a computer system located separate from a medical imaging system. For instance, some or all of the steps of receiving a time series of fluorescence images 112 of the tissue, identifying one or more attributes of the data 114, categorizing the data into a plurality of clusters 116, and further receiving the data for the subject time series of fluorescence images 118, associating the respective cluster with each of the plurality of subregions in the subject time series of fluorescence images 120, generating the subject spatial map 122, and displaying the subject spatial map 122a may be performed by a computer system at an off-site location that is remote from a clinical site (e.g., where a fluorescence imaging system is situated) or by a computer system that is located at a clinical setting but not embodied in an imaging system. In these variations, the time series and/or the subject time series of fluorescence images may be received as a result of a transfer of image data from a data storage medium (e.g., hard drive, cloud storage, etc.) or through a network communication (e.g., wired connection, Internet, wireless network based on a suitable wireless technology standard, etc.). For instance, the method may involve a client-server architecture, such that an imaging system may include client hardware that sends image data to a computing server and loads processed data (e.g., ranking map image or interim outputs of various steps of the methods described herein) back onto the imaging system. After the client hardware in the imaging system loads the processed data, the imaging system may further process the data and/or display the processed data in accordance with the methods described herein.

In some variations, at least a portion of the method is performed by one or more processors at a computer system incorporated into a medical imaging system, such as at a clinical site. For example, some or all of the steps of capturing/receiving a time series of fluorescence images 112 of the tissue and/or receiving data for the subject time series of fluorescence images 118, identifying one or more attributes of the data that are relevant to a clinical characterization of the tissue 114, categorizing the data into a plurality of clusters 116, associating the respective cluster with each of the plurality of subregions in the subject time series of fluorescence images 120, generating the subject spatial map 122, and displaying the subject spatial map 122a may be performed by a computer system in a medical imaging system. In some of these variations, the method may further include generating the time series of fluorescence images 110 prior to receiving the time series of fluorescence images 118.

As described above, conventional medical imaging technologies such as fluorescence imaging technologies provide limited opportunity for clinicians to accurately assess blood flow and/or tissue perfusion in tissue of a subject. For instance, when visually evaluating fluorescence images that capture transit of a dye bolus through tissue, clinicians' assessment of blood flow and/or tissue perfusion is confounded by parameters (e.g., brightness, image contrast, image noise) that are independent of perfusion properties of the tissue. Additionally, clinicians' mere visual evaluation of the images is subjective and may vary from clinician to clinician, patient to patient, and/or imaging session to imaging session.

The methods and systems described herein are useful for characterizing tissue, predicting clinical data or outcomes, and presenting image data to the user in a manner that enables more effective clinical decision making to further facilitate predicting clinical outcomes. In particular, the subject spatial map (e.g., image) generated in accordance with the methods described herein (e.g., 122 in FIG. 1) for a subject (e.g., a patient) undergoing or having undergone medical imaging may be a spatial map that concisely shows relative differences between image elements such as, for example, pixels (or voxels), or relative differences between different regions of imaged subject tissue, with respect to clinically-relevant attributes. In some variations, the subject spatial map (e.g., 122 in FIG. 1) may be a visualization of how different areas of the imaged subject tissue vary in healing status, tissue property, and/or other tissue condition. For example, the subject spatial map image may visualize inflammation, malignancy, disease, or other abnormality of the tissue in a way that is easily perceptible and identifiable by a human being. As further described herein, these generated visualizations reduce ambiguity and the effect of clinicians' subjectivity, by facilitating a standardized protocol for assessing blood flow and/or tissue perfusion and providing a way to compare and track assessments of a subject over time across multiple imaging sessions. Thus, these visualizations enable a clinician to make more consistent clinical assessments and/or medical treatment decisions.

Although various exemplary variations are described herein in the context of a time series and/or a subject time series of fluorescence images, the methods may be applied to other sources of images generated as a time series which relate to a dynamic behavior of an imaging agent in the tissue, and for other clinical purposes. For example, the images may be derived from computerized tomographic (CT) angiography with a radio-opaque contrast dye for blood flow and tissue perfusion assessment. As another example, the images may be derived from positron emission tomography (PET) using a fluorodeoxyglucose (FDG) or other radiotracer to evaluate metabolic activity and potentially assess pathology and/or provide information usable for assessing pathology. As another example, the images may be derived from contrast-enhanced ultrasound imaging employing the use of gas-filled microbubble contrast medium administered intravenously to the systemic circulation. Such ultrasonic imaging using microbubble contrast agents enhances the ultrasound backscatter or reflection of the ultrasound waves to produce a unique sonogram with increased contrast due to the high echogenicity (i.e., ability of an object to reflect the ultrasound waves) difference between the gas in the microbubbles and the soft tissue. Contrast-enhanced ultrasound can be used, for example, to image blood perfusion and blood flow in organs.

Generating the Time Series and the Subject Time Series of Images of the Tissue and Related Data In some variations, as shown in FIG. 1, the method 100 includes generating a time series of fluorescence images 110 of the tissue and/or generating a subject time series of fluorescence images of the subject's tissue 118a prior to receiving the time series 112 and/or the subject time series 118. The time series of fluorescence images and/or the subject time series of fluorescence images may be generated by fluorescence imaging technologies employing a fluorescence imaging agent such as, for example, indocyanine green (ICG) dye as a fluorescence imaging agent. ICG, when administered to the subject, binds with blood proteins and circulates with the blood in the tissue. Although reference is made in the specification to a fluorescence agent or a fluorescence dye, suitable imaging agents other than fluorescence agents or dyes may be used depending on the type of imaging technology being employed to generate the time series of images in variations where the time series of images and/or the subject time series of images is not fluorescence-based.

In some variations, the fluorescence imaging agent (e.g., ICG) may be administered to the subject (e.g., into a vein, an artery, or other tissue) as a bolus injection, in a suitable concentration for imaging. In some variations where the method is performed to assess tissue perfusion, the fluorescence imaging agent may be administered to the subject by injection into a vein or artery of the subject such that the dye bolus circulates in the vasculature and traverses the microvasculature. In some variations in which multiple fluorescence imaging agents are used, such agents may be administered simultaneously (e.g., in a single bolus), or sequentially (e.g., in separate boluses). In some variations, the fluorescence imaging agent may be administered by a catheter. In some variations, the fluorescence imaging agent may be administered to the subject less than an hour in advance of performing the measurements for generating the time series and/or the subject time series of fluorescence images. For example, the fluorescence imaging agent may be administered to the subject less than 30 minutes in advance of the measurements. In other variations, the fluorescence imaging agent may be administered at least 30 seconds in advance of performing the measurements. In some variations, the fluorescence imaging agent may be administered contemporaneously with performing the measurements.

In some variations, the fluorescence imaging agent may be administered in various concentrations to achieve a desired circulating concentration in the blood. For example, in some variations for tissue perfusion assessment where the fluorescence imaging agent is ICG, the fluorescence imaging agent may be administered at a concentration of about 2.5 mg/mL to achieve a circulating concentration of about 5 μM to about 10 μM in blood. In some variations, the upper concentration limit for the administration of the fluorescence imaging agent is the concentration at which the fluorescence imaging agent becomes clinically toxic in circulating blood, and the lower concentration limit is the limit for instruments used to acquire the time series of fluorescence images that detect the fluorescence imaging agent circulating in blood. In some variations, the upper concentration limit for the administration of the fluorescence imaging agent is the concentration at which the fluorescence imaging agent becomes self-quenching. For example, the circulating concentration of ICG may range from about 2 μM to about 10 mM.

Thus, in a variation, the method may comprise administration of a fluorescence imaging agent or other imaging agent to the subject, and generation or acquisition of the time series of fluorescence images and/or the subject time series of fluorescence images prior to processing the generated data. In another variation, the method may exclude any step of administering the fluorescence imaging agent or other imaging agent to the subject. For instance, the time series of fluorescence images and/or the subject time series of fluorescence images may be based on measurements of a fluorescence imaging agent such as, for example, indocyanine green (ICG) dye that is already present in the subject and/or based on autofluorescence response (e.g., native tissue autofluorescence or induced tissue autofluorescence), or measurements of a combination of autofluorescence and exogenous fluorescence arising from a fluorescence imaging agent.

In some variations, a suitable fluorescence imaging agent comprises an agent which can circulate with the blood (e.g., a fluorescence dye which can circulate with a component of the blood such as lipoproteins or serum plasma in the blood) and which fluoresces when exposed to appropriate excitation light energy. The fluorescence imaging agent may comprise a fluorescence dye, an analogue thereof, a derivative thereof, or a combination of these. A fluorescence dye may include any non-toxic fluorescence dye. In some variations, the fluorescence imaging agent optimally emits fluorescence in the near-infrared spectrum. In some variations, the fluorescence imaging agent is or comprises a tricarbocyanine dye such as, for example, indocyanine green (ICG). In other variations, the fluorescence imaging agent is or comprises fluorescein isothiocyanate, rhodamine, phycoerythrin, phycocyanin, allophycocyanin, o-phthaldehyde, fluorescamine, rose Bengal, trypan blue, fluoro-gold, green fluorescence protein, flavins (e.g., riboflavin, etc.), methylene blue, porphysomes, cyanine dyes (e.g., cathepsin-activated Cy5 combined with a targeting ligand, Cy5.5, etc.), IRDye800CW, CLR 1502 combined with a targeting ligand, OTL38 combined with a targeting ligand, methylene blue or a combination thereof, which is excitable using excitation light wavelengths appropriate to each imaging agent. In some variations, the fluorescence imaging agent is or comprises methylene blue, ICG, or a combination thereof. In some variations, an analogue or a derivative of the fluorescence imaging agent may be used. For example, a fluorescence dye analogue or a derivative may include a fluorescence dye that has been chemically modified, but still retains its ability to fluoresce when exposed to light energy of an appropriate wavelength. In variations in which some or all of the fluorescence is derived from autofluorescence, one or more of the fluorophores giving rise to the autofluorescence may be an endogenous tissue fluorophore (e.g., collagen, elastin, NADH, etc.), 5-aminolevulinic acid (5-ALA), or a combination thereof.

In some variations, the fluorescence imaging agent may be provided as a lyophilized powder, solid, or liquid. The fluorescence imaging agent may be provided in a vial (e.g., a sterile vial), which may permit reconstitution to a suitable concentration by administering a sterile fluid with a sterile syringe. Reconstitution may be performed using any appropriate carrier or diluent. For example, the fluorescence imaging agent may be reconstituted with an aqueous diluent immediately before administration. Any diluent or carrier which will maintain the fluorescence imaging agent in solution may be used. As an example, ICG may be reconstituted with water. In some variations, once the fluorescence imaging agent is reconstituted, it may be mixed with additional diluents and carriers. In some variations, the fluorescence imaging agent may be conjugated to another molecule, (e.g., a protein, a peptide, an amino acid, a synthetic polymer, or a sugar) so as to enhance solubility, stability, imaging properties or a combination thereof. Additional buffering agents may optionally be added including Tris, HCl, NaOH, phosphate buffer, HEPES.

A person of skill in the art will appreciate that, although a fluorescence imaging agent was described above in detail, other imaging agents may be used in connection with the systems, methods, and techniques described herein, depending on the medical imaging modality.

In some variations, the fluorescence imaging agent in accordance with one or more of the various embodiments, and used in combination with the methods, systems and kits described herein may be used for blood flow imaging, tissue perfusion imaging, lymphatic imaging, biliary imaging or a combination thereof, which may performed during an invasive surgical procedure, a minimally invasive surgical procedure, a non-invasive surgical procedure, or a combination thereof. Examples of invasive surgical procedure which may involve blood flow and tissue perfusion include a cardiac-related surgical procedure (e.g., CABG on pump or off pump) or a reconstructive surgical procedure. An example of a non-invasive or minimally invasive procedure includes wound (e.g., chronic wound such as for example pressure ulcers) treatment and/or management. In this regard, for example, a change in the wound over time, such as a change in wound dimensions (e.g., diameter, area), or a change in tissue perfusion in the wound and/or around the periwound, may be tracked over time with the application of the methods and systems. Examples of lymphatic imaging include identification of one or more lymph nodes, lymph node drainage, lymphatic mapping, or a combination thereof. In some variations such lymphatic imaging may relate to the female reproductive system (e.g., uterus, cervix, vulva).

In variations relating to cardiac applications or any vascular applications, the imaging agent(s) (e.g., ICG alone or in combination with another imaging agent) may be injected intravenously, or may have been injected intravenously previously. For example, the imaging agent may be injected intravenously through the central venous line, bypass pump and/or cardioplegia line and/or other vasculature to flow and/or perfuse the coronary vasculature, microvasculature and/or grafts. ICG may be administered as a dilute ICG/blood/saline solution down the grafted vessel or other vasculature such that the final concentration of ICG in the coronary artery or other vasculature depending on application is approximately the same or lower as would result from injection of about 2.5 mg (i.e., 1 ml of 2.5 mg/ml) into the central line or the bypass pump. The ICG may be prepared by dissolving, for example, 25 mg of the solid in 10 ml sterile aqueous solvent, which may be provided with the ICG by the manufacturer. One milliliter of the ICG solution may be mixed with 500 ml of sterile saline (e.g., by injecting 1 ml of ICG into a 500 ml bag of saline). Thirty milliliters of the dilute ICG/saline solution may be added to 10 ml of the subject's blood, which may be obtained in an aseptic manner from the central arterial line or the bypass pump. ICG in blood binds to plasma proteins and facilitates preventing leakage out of the blood vessels. Mixing of ICG with blood may be performed using standard sterile techniques within the sterile surgical field. Ten ml of the ICG/saline/blood mixture may be administered for each graft. Rather than administering ICG by injection through the wall of the graft using a needle, ICG may be administered by means of a syringe attached to the (open) proximal end of the graft. When the graft is harvested surgeons routinely attach an adaptor to the proximal end of the graft so that they can attach a saline filled syringe, seal off the distal end of the graft and inject saline down the graft, pressurizing the graft and thus assessing the integrity of the conduit (with respect to leaks, side branches etc.) prior to performing the first anastomosis. In other variations, the methods, dosages or a combination thereof as described herein in connection with cardiac imaging may be used in any vascular and/or tissue perfusion imaging applications.

Lymphatic mapping is an important part of effective surgical staging for cancers that spread through the lymphatic system (e.g., breast, gastric, gynecological cancers). Excision of multiple nodes from a particular node basin can lead to serious complications, including acute or chronic lymphedema, paresthesia, and/or seroma formation, when in fact, if the sentinel node is negative for metastasis, the surrounding nodes will most likely also be negative. Identification of the tumor draining lymph nodes (LN) has become an important step for staging cancers that spread through the lymphatic system in breast cancer surgery for example. LN mapping involves the use of dyes and/or radiotracers to identify the LNs either for biopsy or resection and subsequent pathological assessment for metastasis. The goal of lymphadenectomy at the time of surgical staging is to identify and remove the LNs that are at high risk for local spread of the cancer. Sentinel lymph node (SLN) mapping has emerged as an effective surgical strategy in the treatment of breast cancer. It is generally based on the concept that metastasis (spread of cancer to the axillary LNs), if present, should be located in the SLN, which is defined in the art as the first LN or group of nodes to which cancer cells are most likely to spread from a primary tumor. If the SLN is negative for metastasis, then the surrounding secondary and tertiary LN should also be negative. The primary benefit of SLN mapping is to reduce the number of subjects who receive traditional partial or complete lymphadenectomy and thus reduce the number of subjects who suffer from the associated morbidities such as lymphedema and lymphocysts.

The current standard of care for SLN mapping involves injection of a tracer that identifies the lymphatic drainage pathway from the primary tumor. The tracers used may be radioisotopes (e.g. Technetium-99 or Tc-99m) for intraoperative localization with a gamma probe. The radioactive tracer technique (known as scintigraphy) is limited to hospitals with access to radioisotopes require involvement of a nuclear physician and does not provide real-time visual guidance. A colored dye, isosulfan blue, has also been used, however this dye cannot be seen through skin and fatty tissue. In addition, blue staining results in tattooing of the breast lasting several months, skin necrosis can occur with subdermal injections, and allergic reactions with rare anaphylaxis have also been reported. Severe anaphylactic reactions have occurred after injection of isosulfan blue (approximately 2% of patients). Manifestations include respiratory distress, shock, angioedema, urticarial and pruritus. Reactions are more likely to occur in subjects with a history of bronchial asthma, or subjects with allergies or drug reactions to triphenylmethane dyes. Isosulfan blue is known to interfere with measurements of oxygen saturation by pulse oximetry and methemoglobin by gas analyzer. The use of isosulfan blue may result in transient or long-term (tattooing) blue coloration.

In contrast, fluorescence imaging in accordance with the various embodiments for use in SLN visualization, mapping, facilitates direct real-time visual identification of a LN and/or the afferent lymphatic channel intraoperatively, facilitates high-resolution optical guidance in real-time through skin and fatty tissue, visualization of blood flow, tissue perfusion or a combination thereof.

In some variations, visualization, classification or both of lymph nodes during fluorescence imaging may be based on imaging of one or more imaging agents, which may be further based on visualization and/or classification with a gamma probe (e.g., Technetium Tc-99m is a clear, colorless aqueous solution and is typically injected into the periareolar area as per standard care), another conventionally used colored imaging agent (isosulfan blue), and/or other assessment such as, for example, histology. The breast of a subject may be injected, for example, twice with about 1% isosulfan blue (for comparison purposes) and twice with an ICG solution having a concentration of about 2.5 mg/ml. The injection of isosulfan blue may precede the injection of ICG or vice versa. For example, using a TB syringe and a 30 G needle, the subject under anesthesia may be injected with 0.4 ml (0.2 ml at each site) of isosulfan blue in the periareolar area of the breast. For the right breast, the subject may be injected at 12 and 9 o'clock positions and for the left breast at 12 and 3 o'clock positions. The total dose of intradermal injection of isosulfan blue into each breast may be about 4.0 mg (0.4 ml of 1% solution: 10 mg/ml). In another exemplary variation, the subject may receive an ICG injection first followed by isosulfan blue (for comparison). One 25 mg vial of ICG may be reconstituted with 10 ml sterile water for injection to yield a 2.5 mg/ml solution immediately prior to ICG administration. Using a TB syringe and a 30G needle, for example, the subject may be injected with about 0.1 ml of ICG (0.05 ml at each site) in the periareolar area of the breast (for the right breast, the injection may be performed at 12 and 9 o'clock positions and for the left breast at 12 and 3 o'clock positions). The total dose of intradermal injection of ICG into each breast may be about 0.25 mg (0.1 ml of 2.5 mg/ml solution) per breast. ICG may be injected, for example, at a rate of 5 to 10 seconds per injection. When ICG is injected intradermally, the protein binding properties of ICG cause it to be rapidly taken up by the lymph and moved through the conducting vessels to the LN. In some variations, the ICG may be provided in the form of a sterile lyophilized powder containing 25 mg ICG with no more than 5% sodium iodide. The ICG may be packaged with aqueous solvent consisting of sterile water for injection, which is used to reconstitute the ICG. In some variations the ICG dose (mg) in breast cancer sentinel lymphatic mapping may range from about 0.5 mg to about 10 mg depending on the route of administration. In some variations, the ICG does may be about 0.6 mg to about 0.75 mg, about 0.75 mg to about 5 mg, about 5 mg to about 10 mg. The route of administration may be for example subdermal, intradermal (e.g., into the periareolar region), subareolar, skin overlaying the tumor, intradermal in the areola closest to tumor, subdermal into areola, intradermal above the tumor, periareolar over the whole breast, or a combination thereof. The NIR fluorescent positive LNs (e.g., using ICG) may be represented as a black and white NIR fluorescence image(s) for example and/or as a full or partial color (white light) image, full or partial desaturated white light image, an enhanced colored image, an overlay (e.g., fluorescence with any other image), a composite image (e.g., fluorescence incorporated into another image) which may have various colors, various levels of desaturation or various ranges of a color to highlight/visualize certain features of interest. Processing of the images may be further performed for further visualization and/or other analysis (e.g., quantification). The lymph nodes and lymphatic vessels may be visualized (e.g., intraoperatively, in real time) using fluorescence imaging systems and methods according to the various embodiments for ICG and SLNs alone or in combination with a gamma probe (Tc-99m) according to American Society of Breast Surgeons (ASBrS) practice guidelines for SLN biopsy in breast cancer patients. Fluorescence imaging for LNs may begin from the site of injection by tracing the lymphatic channels leading to the LNs in the axilla. Once the visual images of LNs are identified, LN mapping and identification of LNs may be done through incised skin, LN mapping may be performed until ICG visualized nodes are identified. For comparison, mapping with isosulfan blue may be performed until 'blue' nodes are identified. LNs identified with ICG alone or in combination with another imaging technique (e.g., isosulfan blue, and/or Tc-99m) may be labeled to be excised. Subject may have various stages of breast cancer (e.g., IA, IB, IIA).

In some variations, such as for example, in gynecological cancers (e.g., uterine, endometrial, vulvar and cervical malignancies), ICG may be administered interstitially for the visualization of lymph nodes, lymphatic channels, or a combination thereof. When injected interstitially, the protein binding properties of ICG cause it to be rapidly taken up by the lymph and moved through the conducting vessels to the SLN. ICG may be provided for injection in the form of a sterile lyophilized powder containing 25 mg ICG (e.g., 25 mg/vial) with no more than 5.0% sodium iodide. ICG may be then reconstituted with commercially available water (sterile) for injection prior to use. According to an embodiment, a vial containing 25 mg ICG may be reconstituted in 20 ml of water for injection, resulting in a 1.25 mg/ml solution. A total of 4 ml of this 1.25 mg/ml solution is to be injected into a subject (4×1 ml injections) for a total dose of ICG of 5 mg per subject. The cervix may also be injected four (4) times with a 1 ml solution of 1% isosulfan blue 10 mg/ml (for comparison purposes) for a total dose of 40 mg. The injection may be performed while the subject is under anesthesia in the operating room. In some variations the ICG dose (mg) in gynecological cancer sentinel lymph node detection and/or mapping may range from about 0.1 mg to about 5 mg depending on the route of administration. In some variations, the ICG does may be about 0.1 mg to about 0.75 mg, about 0.75 mg to about 1.5 mg, about 1.5 mg to about 2.5 mg, about 2.5 mg to about 5 mg. The route of administration may be for example cervical injection, vulva peritumoral injection, hysteroscopic endometrial injection, or a combination thereof. In order to minimize the spillage of isosulfan blue or ICG interfering with the mapping procedure when LNs are to be excised, mapping may be performed on a hemi-pelvis, and mapping with both isosulfan blue and ICG may be performed prior to the excision of any LNs. LN mapping for Clinical Stage I endometrial cancer may be performed according to the NCCN Guidelines for Uterine Neoplasms, SLN Algorithm for Surgical Staging of Endometrial Cancer; and SLN mapping for Clinical Stage I cervical cancer may be performed according to the NCCN Guidelines for Cervical Neoplasms, Surgical/SLN Mapping Algorithm for Early-Stage Cervical Cancer. Identification of LNs may thus be based on ICG fluorescence imaging alone or in combination or co-administration with for a colorimetric dye (isosulfan blue) and/or radiotracer.

Visualization of lymph nodes may be qualitative and/or quantitative. Such visualization may comprise, for example, lymph node detection, detection rate, anatomic distribution of lymph nodes. Visualization of lymph nodes according to the various embodiments may be used alone or in combination with other variables (e.g., vital signs, height, weight, demographics, surgical predictive factors, relevant medical history and underlying conditions, histological visualization and/or assessment, Tc-99m visualization and/or assessment, concomitant medications). Follow-up visits may occur on the date of discharge, and subsequent dates (e.g., one month).

Lymph fluid comprises high levels of protein, thus ICG can bind to endogenous proteins when entering the lymphatic system. Fluorescence imaging (e.g., ICG imaging) for lymphatic mapping when used in accordance with the methods and systems described herein offers the following example advantages: high-signal to background ratio (or tumor to background ratio) as NIR does not generate significant autofluorescence, real-time visualization feature for lymphatic mapping, tissue definition (i.e., structural visualization), rapid excretion and elimination after entering the vascular system, and avoidance of non-ionizing radiation. Furthermore, NIR imaging has superior tissue penetration (approximately 5 to 10 millimeters of tissue) to that of visible light (1 to 3 mm of tissue). The use of ICG for example also facilitates visualization through the peritoneum overlying the para-aortic nodes. Although tissue fluorescence can be observed with NIR light for extended periods, it cannot be seen with visible light and consequently does not impact pathologic evaluation or processing of the LN. Also, florescence is easier to detect intra-operatively than blue staining (isosulfan blue) of lymph nodes. In other variations, the methods, dosages or a combination thereof as described herein in connection with lymphatic imaging may be used in any vascular and/or tissue perfusion imaging applications.

Tissue perfusion relates to the microcirculatory flow of blood per unit tissue volume in which oxygen and nutrients are provided to and waste is removed from the capillary bed of the tissue being perfused. Tissue perfusion is a phenomenon related to but also distinct from blood flow in vessels. Quantified blood flow through blood vessels may be expressed in terms that define flow (i.e., volume/time), or that define speed (i.e., distance/time). Tissue blood perfusion defines movement of blood through micro-vasculature, such as arterioles, capillaries, or venules, within a tissue volume. Quantified tissue blood perfusion may be expressed in terms of blood flow through tissue volume, namely, that of blood volume/time/tissue volume (or tissue mass). Perfusion is associated with nutritive blood vessels (e.g., micro-vessels known as capillaries) that comprise the vessels associated with exchange of metabolites between blood and tissue, rather than larger-diameter non-nutritive vessels. In some embodiments, quantification of a target tissue may include calculating or determining a parameter or an amount related to the target tissue, such as a rate, size volume, time, distance/time, and/or volume/time, and/or an amount of change as it relates to any one or more of the preceding parameters or amounts. However, compared to blood movement through the larger diameter blood vessels, blood movement through individual capillaries can be highly erratic, principally due to vasomotion, wherein spontaneous oscillation in blood vessel tone manifests as pulsation in erythrocyte movement.

In some variations, upon interstitial administration, the fluorescence imaging agent, e.g., ICG, may be used for fluorescence imaging of lymph nodes and delineation of lymphatic vessels in the cervix and uterus during lymphatic mapping in patients with solid tumors for which this procedure is a component of intraoperative management. The fluorescence agent, e.g., ICG, may be used, for example, with the PINPOINT® fluorescence imaging system (available from Novadaq Technologies Inc.) to perform intraoperative fluorescence imaging during lymphatic mapping.

In some variations, upon intradermal administration, the fluorescence imaging agent, e.g., ICG, may be used for fluorescence imaging of lymph nodes and delineation of lymphatic vessels in the breast during lymphatic mapping in patients with solid tumors for which such a procedure is a component of intraoperative management. The fluorescence agent, e.g., ICG, may be used, for example, with the SPY-PHI portable handheld imaging system (available from Novadaq Technologies Inc.) to perform intraoperative fluorescence imaging during lymphatic mapping.

In some variations, upon intradermal (including subcutaneous) administration, the fluorescence imaging agent, e.g., ICG, may be used for fluorescence imaging of lymph nodes and delineation of lymphatic vessels in cutaneous tissue during lymphatic mapping in patients with solid tumors for which this procedure is a component of intraoperative management (e.g., melanoma). The fluorescence imaging agent, e.g., ICG, may be used, for example, with the SPY® Elite and SPY-PHI portable handheld imaging systems (available from Novadaq Technologies Inc.) to perform intraoperative fluorescence imaging during lymphatic mapping.

In some variations, upon interstitial administration, the fluorescence imaging agent, e.g., ICG, may be used for fluorescence imaging of lymph nodes and delineation of lymphatic vessels during lymphography in primary and secondary lymphedema of the extremities. The fluorescence imaging agent, e.g., ICG, may be used, for example, with the SPY® Elite and SPY-PHI portable handheld imaging systems (available from Novadaq Technologies Inc.) to perform intraoperative fluorescence imaging during lymphatic mapping.

In some variations, upon intravascular administration, the fluorescence imaging agent, e.g., ICG, may be used for fluorescence imaging of blood flow and tissue perfusion during vascular, and/or organ transplant surgeries. The fluorescence imaging agent, e.g., ICG, may be used with the SPY® Elite, LUNA and SPY-PHI fluorescence imaging systems (available from Novadaq Technologies Inc.) to perform intraoperative fluorescence imaging (e.g., angiography).

In some variations, upon intravascular administration, fluorescence imaging agent, e.g., ICG, may be used for fluorescence imaging of blood flow and tissue perfusion during vascular, gastrointestinal, organ transplant, plastic, micro-, and/or reconstructive surgeries, including general minimally invasive surgical procedures. The fluorescence imaging agent, e.g., ICG, may be used with the SPY® Elite, LUNA, SPY-PHI and PINPOINT® fluorescence imaging systems (available from Novadaq Technologies Inc.) to perform intraoperative fluorescence imaging (e.g., angiography).

In some variations, upon intravascular administration, fluorescence imaging agent, e.g., ICG, may be used for fluorescence imaging of biliary ducts, and during intraoperative cholangiography. The fluorescence imaging agent, e.g., ICG, may be used with the PINPOINT® fluorescence imaging system (available from Novadaq Technologies Inc.) to perform such imaging.

One or more embodiments are directed to a fluorescence imaging agent for use in the imaging systems and methods as described herein. In one or more embodiments, the use may comprise blood flow imaging, tissue perfusion imaging, lymphatic imaging, or a combination thereof, which may occur during an invasive surgical procedure, a minimally invasive surgical procedure, a non-invasive surgical procedure, or a combination thereof. The fluorescence agent may be included in the kit described herein.

In one or more embodiments, the invasive surgical procedure may comprise a cardiac-related surgical procedure or a reconstructive surgical procedure. The cardiac-related surgical procedure may comprise a cardiac coronary artery bypass graft (CABG) procedure which may be on pump and/or off pump.

In one or more embodiments, the minimally invasive or the non-invasive surgical procedure may comprise a wound care procedure.

In one or more embodiments, the lymphatic imaging may comprise identification of a lymph node, lymph node drainage, lymphatic mapping, or a combination thereof. The lymphatic imaging may relate to the female reproductive system.

The methods and processes described herein may be performed by code or instructions to be executed by a computer, processor, manager, or controller, or in hardware or other circuitry. Because the algorithms that form the basis of the methods (or operations of the computer, processor, or controller) are described in detail, the code or instructions for implementing the operations of the method embodiments may transform the computer, processor, or controller into a special-purpose processor for performing the methods described herein.

Also, another embodiment may include a computer-readable medium, e.g., a non-transitory computer-readable medium, for storing the code or instructions described above. The computer-readable medium may be a volatile or non-volatile memory or other storage device, which may be removably or fixedly coupled to the computer, processor, or controller which is to execute the code or instructions for performing the method embodiments described herein.

In some variations, the time series of fluorescence images and/or the subject time series of fluorescence images comprises a plurality of individual image frames (e.g., fluorescence image frames), or data representative of individual frames, ordered consecutively by acquisition time. For example, the time series of fluorescence images and/or the subject time series of fluorescence images can be acquired using a fluorescence imaging system, where the subject receives an intravenous injection of ICG immediately prior to procedure, and the tissue is illuminated with light at ICG's excitation wavelengths while the resulting fluorescence emission from the dye as it transits the target tissue is imaged. The fluorescence images may subsequently also stored as a series of individual frames, or data representative of individual frames (e.g., compressed video), ordered consecutively by their acquisition time.

In some variations, the individual image frames of the time series are spatially aligned or registered. For example, a typical time series of fluorescence images and/or the subject time series of fluorescence images may be recorded over 2 to 3 minutes, during which some subject's movements may be unavoidable. As a result, the same anatomical features can appear at different positions in image frames acquired at different times during the image time series acquisition period. Since such misalignments can introduce errors in the subsequent analysis where the level of fluorescence for each pixel or a group of pixels is followed over time. To help reduce errors, the generated image frames may be spatially aligned (registered) with each other. In some variations, image registration or alignment refers to a process of determining the spatial transform that maps points from one image to homologous points in the second image.

Image registration may be an iterative process. For example, according to an exemplary embodiment, image registration may use one or more of the following set of components: two input images, a transform, a metric, an interpolator, and an optimizer. A transform maps the fixed image space into the moving image space. An optimizer is required to explore the parameter space Insight Segmentation and Registration Toolkit (ITK) (http://itk.org/) based implementation of the transform in search of optimal values of the metric may be used. The metric compares how well the two images match each other. Finally, the interpolator evaluates the intensities of the moving image at non-grid positions. To align the entire time series of fluorescence images, this procedure is executed for all the frames included in the analysis. The component loops through the range of input series frames, subtracts a background image for baseline correction and applies noise-reduction filters, then registers consecutive pairs of images.

In some variations, the data for a plurality of time series of fluorescence images and/or the subject time series of fluorescence images, which includes image data, may comprise raw data, preprocessed data, or a combination thereof. In some variations, the time series of fluorescence images and/or the subject time series of fluorescence images is pre-processed to, for example, extract selected data, calculate a baseline intensity, perform an image quality improvement process, or a combination thereof.

Extraction of selected data may, for example, comprise cropping to locate and exclude certain data from the image time series data. For example, during a fluorescence imaging procedure of the subject, an operator might start recording the time series of fluorescence images and/or the subject time series of fluorescence images well before the fluorescence imaging agent reaches the target tissue. As a result, the time series of fluorescence images might have a significant number of "dark" frames in the beginning, thus adding unnecessary computational time for the frames that contain no meaningful data. To mitigate the problem, cropping can be used to remove those "dark" frames from the beginning of the time series of fluorescence images. In addition, when the subject is injected with the fluorescence imaging agent (e.g., ICG), the fluorescence signal from the imaging agent as it transits the target tissue typically proceeds through a series of phases: rapid increase of fluorescence intensity as the imaging agent enters the tissue through arterial vessels, followed by a period of stable fluorescence as the imaging agent traverses the microvasculature, then slow decrease in fluorescence intensity due to the venous outflow of the imaging agent, followed by a period of residual fluorescence as any imaging agent retained in the lining of the vasculature released into the bloodstream. This last "residual" phase can last for several minutes and, as it is not directly indicative of blood flow, does not typically provide meaningful perfusion information. Thus, cropping may be used to locate and exclude the residual phase from subsequent steps of analysis.

In some variations, pre-processing may include calculation of the baseline intensity. For example, when the time series of fluorescence images and/or the subject time series of fluorescence images is being generated by a fluorescence imaging system, various external factors can contribute to the fluorescence of the recorded series, such as camera noise, thermal noise, and/or presence of residual fluorescence dye from an earlier injection. In order to minimize the influence of such factors on the analysis, the baseline intensity may be calculated for every series, and the analysis of the data may be adjusted accordingly.

In some variations, pre-processing may include an image quality validation process. Such a process may comprise a starting brightness test in embodiments where, for example, the acquisition of the time series of fluorescence images has started too late and the imaging agent has already begun its transit of the target tissue by the time the first frame was captured. In this scenario, the time series of fluorescence images cannot be reliably analyzed or processed since the information relating to the start of perfusion has been lost. As a result, such series data would be rejected.

In some variations, the image quality validation process may comprise a brightness change test. Such a test may be used, for example, in instances where the fluorescence imaging system was suddenly moved during the image acquisition, foreign objects appeared in the field of view, or a light from an external source illuminated the scene while the series was being captured. All of these events may significantly distort the results of any subsequent analysis. Accordingly, the time series of fluorescence images subjected to such a test might fail the validation procedure (be identified as being unsuitable for further processing). According to an exemplary embodiment, the brightness change test comprises a calculation of the difference between average intensities of neighboring frames in the time series of fluorescence images and compares it to a selected intensity difference threshold. In order to pass validation, the differences in intensities of all consecutive frames must be within the limit specified by the selected intensity difference threshold.

In some variations, the image quality validation process may comprise an intensity peak location test to check that the acquisition of the time series of fluorescence images has not been stopped prematurely. For example, the intensity peak location test ensures that a sufficient number of frames have been acquired to cover all phases of the dye bolus transit through the tissue. According to an exemplary embodiment, the fluorescence intensity peak location test comprises finding the frame with the maximum average fluorescence intensity and verifying that it is not the last frame in the time series of fluorescence images. Should this condition fail, it will be a strong indication that the fluorescence intensity values have not reached their maximum yet and such a time series of fluorescence images is not suitable for further analysis.

In some variations, the image quality validation process may yet further comprise a maximum fluorescence intensity test. The purpose of the test is to filter out the time series of fluorescence images in which the images are too dark (majority of pixels fall below a pre-defined threshold) or over-saturated (majority of pixels are above a pre-defined saturation threshold).

The curvature of the tissue surface, excessive movement during the image acquisition procedure, dark or oversaturated images, foreign objects within imaged area and external light or shading can affect the quality of the time series of fluorescence images and/or the subject time series of fluorescence images, and thus the subsequent processing of such image data. To mitigate these problems, a well-structured imaging protocol and a fluorescence imaging system designed to minimize such issues may be used.

In some variations, the data may be also preprocessed by applying, for example, data compression, principal component analysis, autoencoding, or a combination of these approaches, or other preprocessing known in the art. The preprocessing may vary depending on the type of data and/or imaging application. In some variations, the preprocessing may comprise calculation of a coefficient, spatial position, onset time, time to blush, maximum fluorescence intensity, ingress of blood, egress of blood, or a combination thereof.

Attributes of Data Relevant to Clinical Characterization of Tissue

As shown in FIG. 1, the illustrated method includes identifying one or more attributes of the data (e.g., fluorescence imaging-derived data) that are relevant to a clinical characterization of the tissue. In some variations, the one or more attributes of the data for the plurality of time series of fluorescence images (e.g., 114 in FIG. 1) comprises a plurality of time-intensity curves for the plurality of subregions or calculation regions in the time series of fluorescence images. Each time-intensity curve corresponds to a respective subregion or calculation region in the fluorescence images. In some variations, at least one of the subregions or calculation regions may be an image element such as, for example, a single pixel or group of pixels, a voxel or group of voxels, or some other spatially defined area or volume in the time series of fluorescence images. Each subregion or calculation region may be identical in size to all other subregions or calculation regions, or may be different in size compared to some or all other subregions or calculation regions. In one variation, the boundaries and/or distribution of one or more subregions or calculation regions may be pre-defined (e.g., a calculation region for each pixel or voxel, or a calculation region for each 2×2 group of pixels or 2×2×2 block of voxels). In another variation, the boundaries and/or distribution of one or more subregions or calculation regions may be defined by a user such as the clinician.

For each of some or all of the plurality of subregions or calculation regions, an individual time-intensity curve may be generated. As shown schematically in FIGS. 2A and 2B, a given time-intensity curve 212 (FIG. 2B) corresponding to a particular subregion or calculation region 210 (FIG. 2A) describes the intensity of fluorescence signal observed in that subregion or calculation region throughout the time series of fluorescence images of the tissue (i.e., with time). In some variations, a time-intensity curve describes all phases (e.g. arterial, micro-vascular, venous and residual in angiography applications), a subset of a phase or of a combination of phases, a subset of all phases, or a derivative thereof (including, for example, determinations based upon first and second time derivatives associated with changes in fluorescent intensity on a pixel-by-pixel, or voxel-by-voxel, basis). All or some of the time-intensity curves may be generated by a processor embodied in a fluorescence imaging system that generated the fluorescence images of the tissue, or by a processor remote from the fluorescence imaging system that generated the fluorescence images.

In some variations, as shown in FIG. 2B, a time-intensity curve 212 comprises a region of increasing intensity, a region of peak intensity, a plateau region, a region of decreasing intensity, or a combination thereof. In the context of fluorescence imaging (e.g., fluorescence angiography), as shown in FIG. 3, a time-intensity curve 312 may represent the transit of a fluorescence imaging agent (e.g., a fluorescence dye) bolus through the tissue as a series of phases: an arterial phase, a micro-vascular phase, a venous phase, a residual phase, or a combination thereof.

The shape of the time-intensity curve (or a portion thereof), an area under the time-intensity curve, or a combination thereof may be indicative of distribution of the fluorescence imaging agent in the tissue of the subject, blood flow in the tissue, or a combination thereof. In some applications, the distribution of the imaging agent in the tissue of the subject represents a property of the tissue, a condition of the tissue (e.g., inflammation, malignancy, abnormality, disease) or a combination thereof.

In some variations, the one or more attributes of the data for the plurality of time series of fluorescence images (e.g., 114 in FIG. 1) may comprise the time-intensity curve as described herein, a coefficient, spatial position, onset time, time to blush, maximum fluorescence intensity, ingress of blood, egress of blood, or a combination thereof for the plurality of subregions or calculation regions in the time series of fluorescence images. In further variations, the one or more attributes of the data for the plurality of time series of fluorescence images may comprise contributions of neighboring pixels (e.g., statistical properties), intensity gradients in space and time, or a combination thereof.

In some variations, the plurality of time series of fluorescence images (e.g., 112) may be derived from a healthy subject, a population of healthy subjects, a healthy tissue region in the target tissue of the subject, a healthy tissue region outside the target tissue of the subject, a combination of two or more of such alternatives, or a further combination of such alternatives taking into account, in some variations, the background in the time series of fluorescence images. Furthermore, the time series of fluorescence images (e.g., 112) may be specific for a particular modality (e.g. a systemic condition such as diabetes), a condition, a clinical context or a combination of these factors within which the tissue (e.g., wound tissue) is being assessed.

Categorization of the Data into Clusters

As shown in FIG. 1, the method includes categorizing the data into a plurality of clusters based on the one or more attributes of the data such that the data in the same cluster are more similar to each other than the data in different clusters, wherein the clusters characterize the tissue 116. The number of clusters into which the data is categorized may be optimized and determined for a particular application. In some variations, the categorization of the data into the plurality of clusters comprises categorizing the data into a selected number of clusters (e.g., ten or fewer clusters).

Figure 3B:
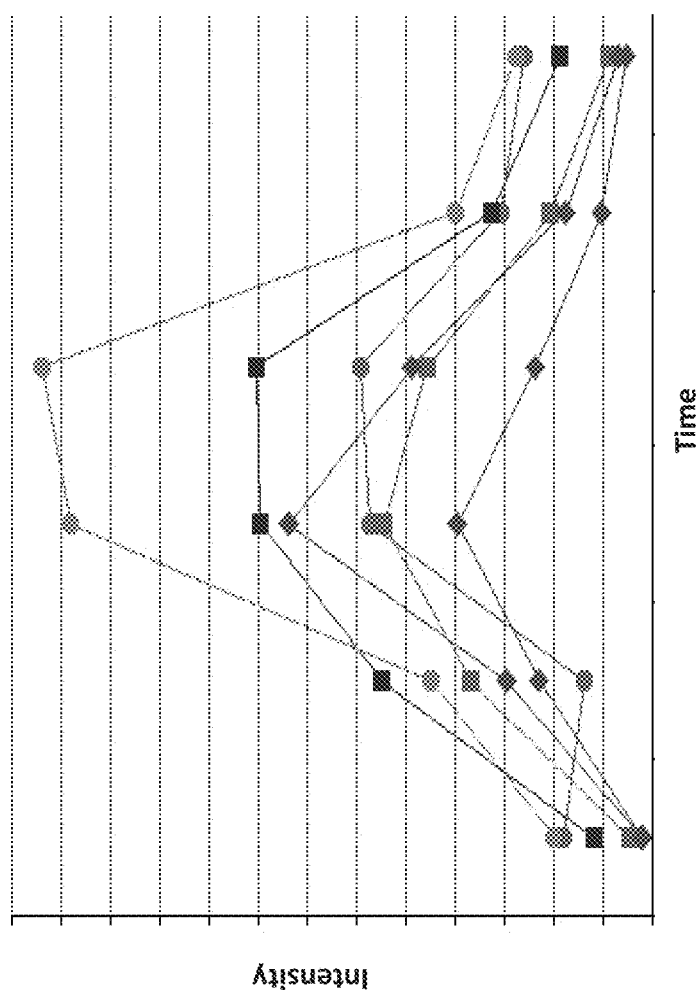
FIG. 3B illustrates a sample dataset comprising a plurality of intensity vs. time curves for individual pixels where the intensity values over time comprise the feature vector.
Figure 3C:
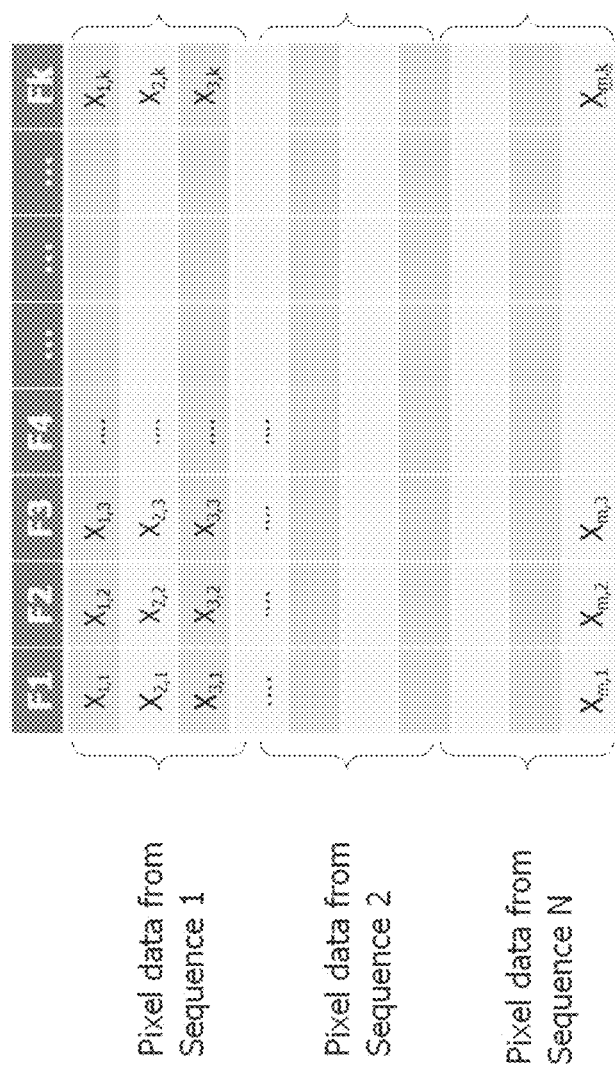
FIG. 3C illustrates a combination of pixel entries from various training sequences into a single matrix.
Figure 3E:
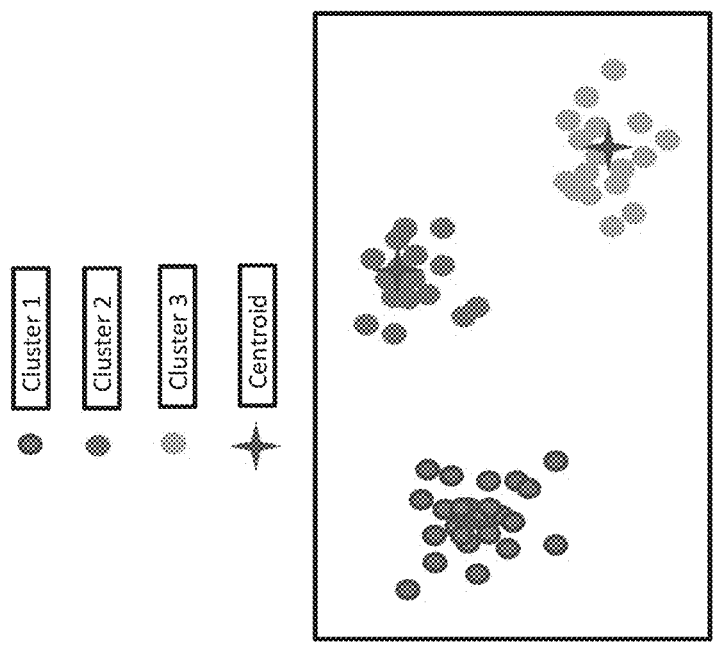
FIG. 3D and FIG. 3E illustrates schematically categorization of the pixel curves and assignment of a label to each data sample.
Figure 3D:

In some variations, when the data for the plurality of time series of fluorescence images is received, a feature vector for the data may be selected, each feature vector characterizing one or more features of the data, and a dataset comprising the feature vectors may be generated. For example, for a selected imaging modality (or modalities) (e.g., chronic wounds, acute wounds, pressure ulcers), for a selected anatomical feature(s) (e.g., foot, heel, shin, breast, etc.) or a combination thereof, a user may choose a number of representative field sequences (e.g., approximately 3-5) that cover a wide range of tissue conditions (e.g., wounds) and their different stages. For example, in a time series of fluorescence images of the tissue, since every field sequence can be treated as 3D data (2 space dimensions and 1 temporal dimension), one can utilize the temporal dimension and use the individual pixel's intensity vs time curves (time-intensity curves) as feature vectors for generating a dataset. This approach facilitates overcoming the 'big data' requirement posed by conventional technologies utilizing machine learning algorithms. Fluorescence imaging systems, such as for example a SPY® fluorescence imaging system, SPY-PHI fluorescence imaging system, PIN-POINT® fluorescence imaging system, and LUNA® fluorescence imaging system all available from Novadaq Technologies Inc., record sequences of frames, where each sequence can generate millions of pixels. As a result, every individual pixel (or calculation region as described herein) represents a single sample of the dataset, while its intensity values over time comprise the feature vector. Thus, the dataset comprises a collection of intensity vs. time curves as is illustrated in FIG. 3B. In some variations, as is illustrated in FIG. 3C, the dataset may be generated by combining pixel entries from different training sequences into a single matrix.

One of the challenges in interpretation and processing of data derived from time series of fluorescence imaging, where for example, the time intensity curve is selected as an attribute relevant to a clinical characterization of the tissue is finding an accurate and consistent way of classifying the time intensity curves. It is known in the art that the dynamic of blood flow and/or perfusion through the tissue is directly correlated with its survivability and healing potential. As a result, it is desirable to establish what represents a meaningful difference or differentiation in the multitude of observed intensity vs. time curves, and what can be disregarded as noise. The methods and systems described herein remove the 'human factor', and thus facilitate identification of blood flow and/or perfusion patterns that appear highly correlated with the health of the imaged tissue.

In some variations, an algorithm is utilized to categorize the clusters, which facilitates finding a natural grouping in data such that items in the same cluster are more similar to each other than those from different clusters. The categorization comprises, for example, splitting the dataset into several different categories of pixel curves (e.g., FIG. 3D), and subsequently assigning each data sample its proper label. To achieve that, a known unsupervised learning clustering (partitioning) algorithm, e.g. K-means++, may be employed. In further variations, other clustering algorithms can be employed instead of K-means, such as Density-based Spatial Clustering of Applications with Noise (DBSCAN) or hierarchical clustering (agglomerative or divisive). In some variations, each cluster is represented by a centroid (e.g., FIG. 3E). The 2-dimensional scatter graphs do not show the curves, but rather, they serve as a visualization aid only. Depending on the application, one or more of such clustering techniques may be used. For example, a hierarchical clustering method may be first used to split the subjects into different demographics, and then density-based clustering may be applied to perfusion data derived from such subjects.

Figure 3F:
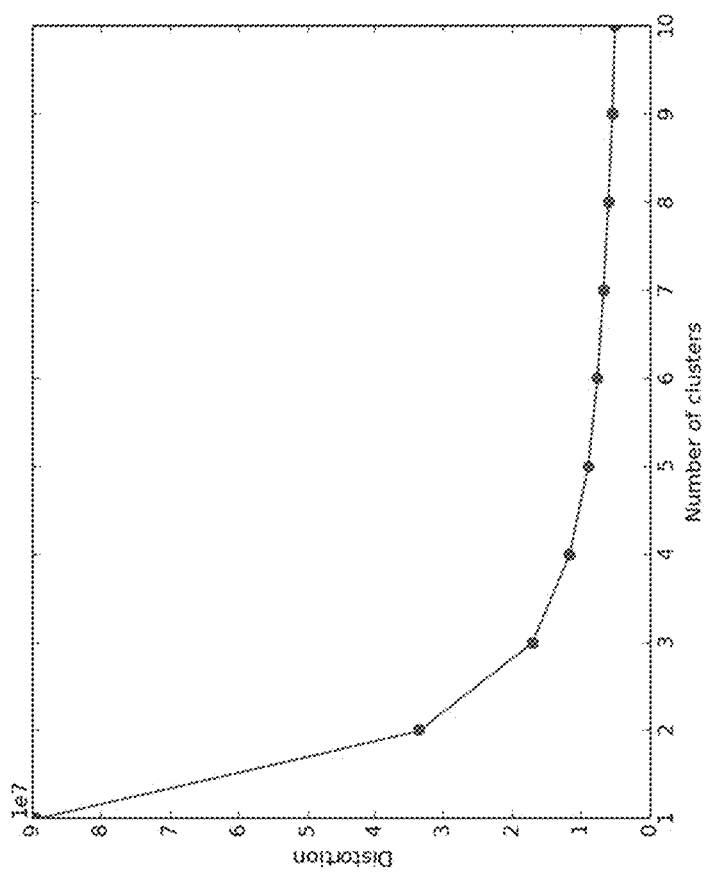
FIG. 3F illustrates determination of an optimal number of clusters for the categorization.

One of the challenges in unsupervised learning is that it does not utilize labels in the dataset, unlike the supervised learning approach, that allow evaluating the performance of the model. Thus, in order to quantify the quality of clustering, intrinsic metrics may be used to compare the performance of different K-means clusterings. A graphical tool may be employed (e.g., the so-called elbow method) to estimate the optimal number of clusters, k, for a given task. If k increases, the distortion will probably decrease because the samples will be closer to the centroids they are assigned to. The idea behind the elbow method is to identify the value of k where the distortion begins to increase most rapidly, as becomes clearer by plotting distortion for different values of k. This is illustrated, for example, in FIG. 3F, where in order to determine what would be the optimal number of curve classes, the cumulative classification error (distortion) is calculated for the range of cluster numbers from 1 to 10 and plotted as a graph for easy visualization. The graph in FIG. 3F illustrates that after reaching 5-6 clusters, the distortion curve plateaus. Therefore, in this particular exemplary context for the data, an inference may be drawn that all the pixel-based intensity vs time curves can be roughly grouped into 7 different categories with a minimal impact on overall accuracy.

Following the determination of the optimal number of clusters, the algorithm may be applied to the training set again using this number as an input parameter. The output of the algorithm will be a trained model which can predict the label (i.e., cluster ID) of any feature vector comprising the same attributes as the feature vectors used in the training dataset. The model may also be polled to output the centroids used for labeling. After the trained model has been generated successfully, it can be used for labeling pixel curves in new sequences, thus facilitating generating a false-color spatial map (cluster) representing curve distribution in the imaged tissue.

Deriving Clinically Relevant Information about the Tissue from the Categorized Clusters In some variations, the clusters themselves may provide valuable information about the tissue. For example, the clusters may characterize the tissue based on spatial distribution of the clusters, properties of the clusters, cluster data, or a combination thereof. In some variations, the properties of the clusters comprise shape of the clusters.

In some variations, the categorized clusters may be converted into a spatial map 116a (FIG. 1) showing the distribution of the clusters, and thereby visualizing any relative differences among the subregions or calculation regions in the time series of fluorescence images, representing differences in blood flow, perfusion patterns, or a combination thereof among a plurality of subregions in the time series of fluorescence images. Thus, the categorized clusters may show any relative differences among different parts of the imaged tissue with respect to the one or more identified attributes of the data relevant to the clinical characterization of the tissue. This may facilitate highlighting different properties (e.g., physiological properties) of the tissue in an objective, easily understood manner. As further described above, as a result, the categorized clusters may facilitate more effective, consistent clinical assessments and decision-making.

In some variations, the centroid values for the clusters may be mapped to a gray scale or a color scale value, for example, an 8-bit grayscale display value (e.g., from 0 to 255), allowing for a grayscale image representation of the centroids. In some variations, to optimize visual perception, a color scheme can be applied to the grayscale image representation with different grayscale value ranges represented in appropriately contrasting colors (such as a false color or pseudo color). Other scales may additionally or alternatively be applied to convert the centroids into pixel values for the spatial map image 116a, such that the differences in pixel values reflect the relative differences among different regions of the imaged tissue from which the data is derived.

In further variations, the categorized cluster data may be compiled into other forms including graphical and mathematical characterizations, calculation of a percentage of curves with a particular cluster label, calculation of statistics about the spatial map (cluster map) built including, for example, histograms, standard deviation about the labels, or a combination thereof. In some variations, the centroids themselves may represent a particular clinical condition (e.g., venous occlusion), and may be used by a clinician to diagnose a clinical condition for a particular subject whose data is correlated with a particular centroid.

Displaying the Spatial Map of the Clusters and Other Steps

In some variations, as shown in FIG. 1, the method may further include displaying the spatial map image 116b on a display. For example, the spatial map image may be displayed within a user interface on a video monitor in a fluorescence imaging system, or other suitable display. The spatial map image may be displayed alone, or in combination with another image (e.g., overlaid with or superimposed on an anatomical image) or other data. Such other data may relate, for example, to a systemic or local condition of the subject or a population of subjects providing a particular clinical context for that subject and/or population of subjects. Such a condition may comprise a comorbid condition including, for example, hypertension, dyslipidemia, diabetes mellitus, chronic obstructive pulmonary disease, coronary artery disease, chronic kidney disease, or a combination thereof. In some variations, the spatial map image may be displayed with other data or metadata relating to the subject, population of subject, the tissue, or a combination thereof as described further below.

In some variations, the method may further comprise correlating the clusters and/or the spatial map with a risk estimate for clinically relevant (e.g., tissue perfusion-related) condition. Such assessments may be made pre-intervention, during treatment/procedure, and post-intervention. The method may also comprise, based on the clusters, defining a diagnosis to identify and characterize a clinically relevant (e.g., tissue perfusion-related) condition in the subject pre-intervention, during treatment/procedure, and post-intervention. In other variations, the method may exclude the correlation and diagnoses steps.

Using the Clusters for Characterization of Subject Time Series of Florescence Images or Other Data of Tissue of a Subject In some variations, the method may further comprise training a machine learning model based on the categorized data. In some variations, the machine learning model may be trained in a machine learning algorithm. As is shown in FIG. 1, following the clustering, the method may further comprise receiving data for a subject time series of fluorescence images of the subject 118, associating a respective cluster with each of a plurality of subregions in the subject time series of fluorescence images 120, and generating a subject spatial map based on the associated clusters for the plurality of subregions in the subject time series of fluorescence images 122.

Generation of the subject spatial map may be performed in a manner similar to what was described above in connection with the generation of the spatial map 116a. For example, generating the subject spatial map may comprise assigning at least one of an intensity value and a color to each subregion in the subject time series of fluorescence images, based on the associated cluster.

Unlike unprocessed data for a subject time series of fluorescence images with their wide continuous range of intensity/color values, the subject spatial map (e.g., 122 in FIG. 1; 422 in FIG. 4) is based on highly-structured discreet set of parameters. As a result, any clinically relevant flow patterns and/or perfusion patterns may be more easily detected by trained neural networks that are customarily used for the tasks of image classification. The flow patterns and/or perfusion patterns revealed by the subject spatial map can be predictive of various clinical conditions that are otherwise not evident to a human observer. By training a specially-designed neural network on a large number of labeled subject spatial maps as input, a predictive machine learning framework may be built capable of automatically identifying clinically relevant conditions in the imaged tissue. Various learning models may be used for predictive analytics of the tissue (e.g., wound healing time predictor) including, for example, information-based learning (decision trees and their ensembles), similarity-based learning (k-nearest neighbors algorithm), probability-based learning (Bayesian networks), error-based learning (logistic regression, support vector machines, artificial neural networks), or a combination thereof.

Figure 4:
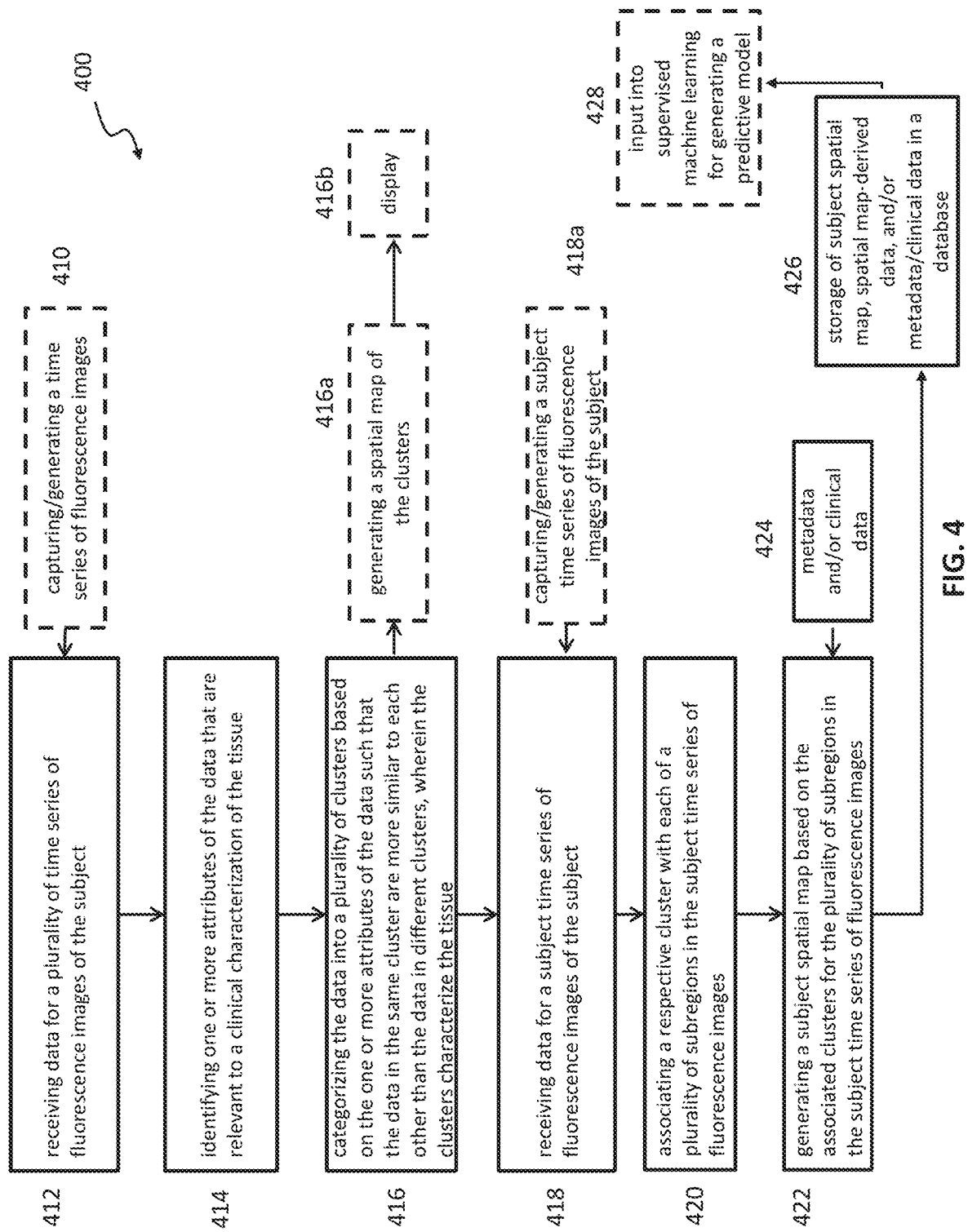
FIG. 4 is an illustrative block diagram of an exemplary method for characterizing tissue of a subject in a variation.

In some variations, e.g. shown in FIG. 4, an example method 400 may be used for predicting clinical data, where the method 400 comprises generating a subject spatial map based on the associated clusters (e.g., steps 410 through 422 in FIG. 4 which may generally correspond to steps 110 through 122 in FIG. 1), receiving metadata associated with each subject spatial map 424, storing each subject spatial map and its associated metadata in a record of a database 426. The method may further comprise using the records of the database as input for a machine learning algorithm, e.g. a supervised machine learning algorithm, for generating a predictive model 428.

In some variations, the metadata may comprise clinical data, non-clinical data, or a combination thereof. The clinical data may comprise, for example, subject health history (e.g., co-morbidities, smoking etc.), subject vital statistics (e.g., blood pressure, temperature etc.), a diagnosis of a tissue abnormality, predicted healing time in a wound, suggested treatment plan, mechanical metrics associated with wound size/shape, presence/absence and properties of granulation tissue formation, oxygenation status of wound and/or periwound, infection status of wound and/or peri-wound, or combination thereof. The non-clinical data may comprise the subject's age, heritage, visit number, or a combination thereof. In some variations, the metadata may be weighed accordingly relative to other factors (e.g., depending on the importance of each parameter). Furthermore, in some variations, the weighting applied may be modulated as each input is better understood.

Figure 5A:
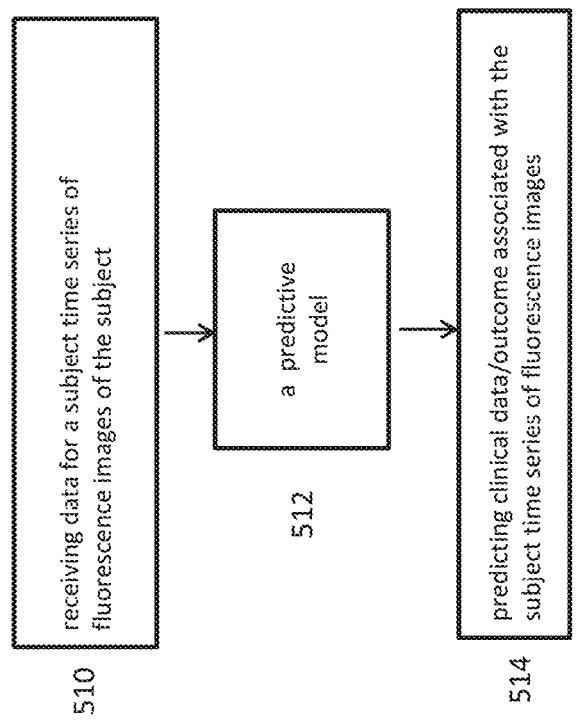
FIG. 5A is an illustrative block diagram of an exemplary method for predicting clinical data.
Figure 5B:
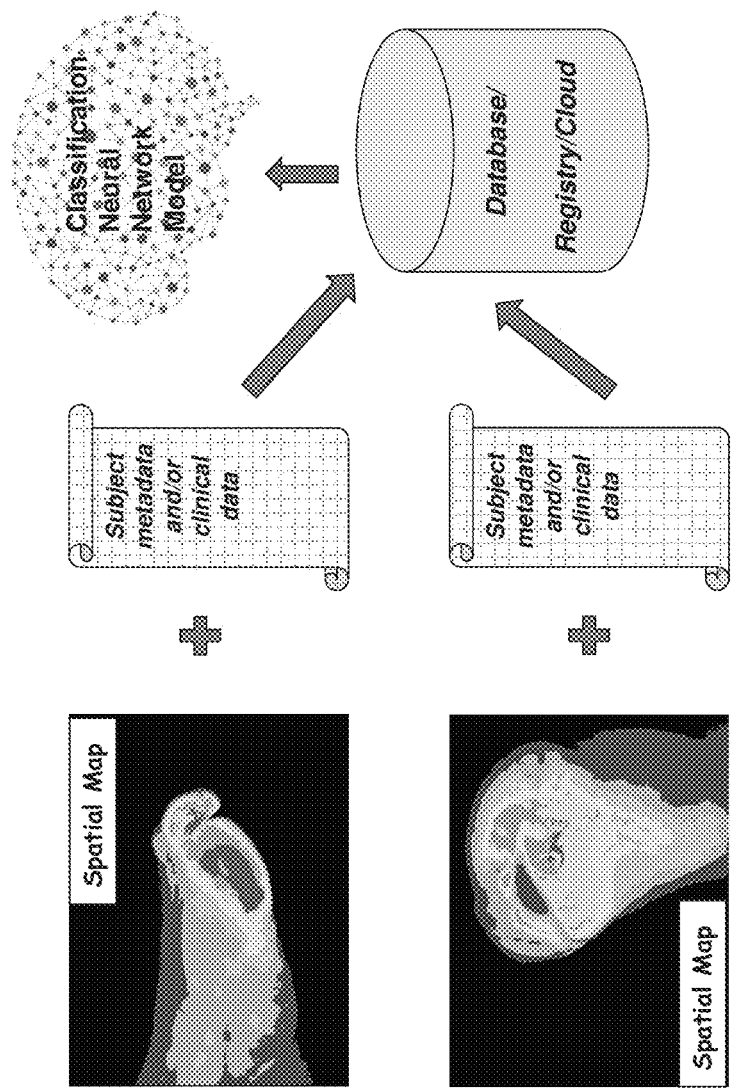
FIG. 5B is an illustrative diagram of using the spatial maps in combination with subject metadata/clinical data as input into a database or a registry, and further in a classification neural network training.
Figure 5C:
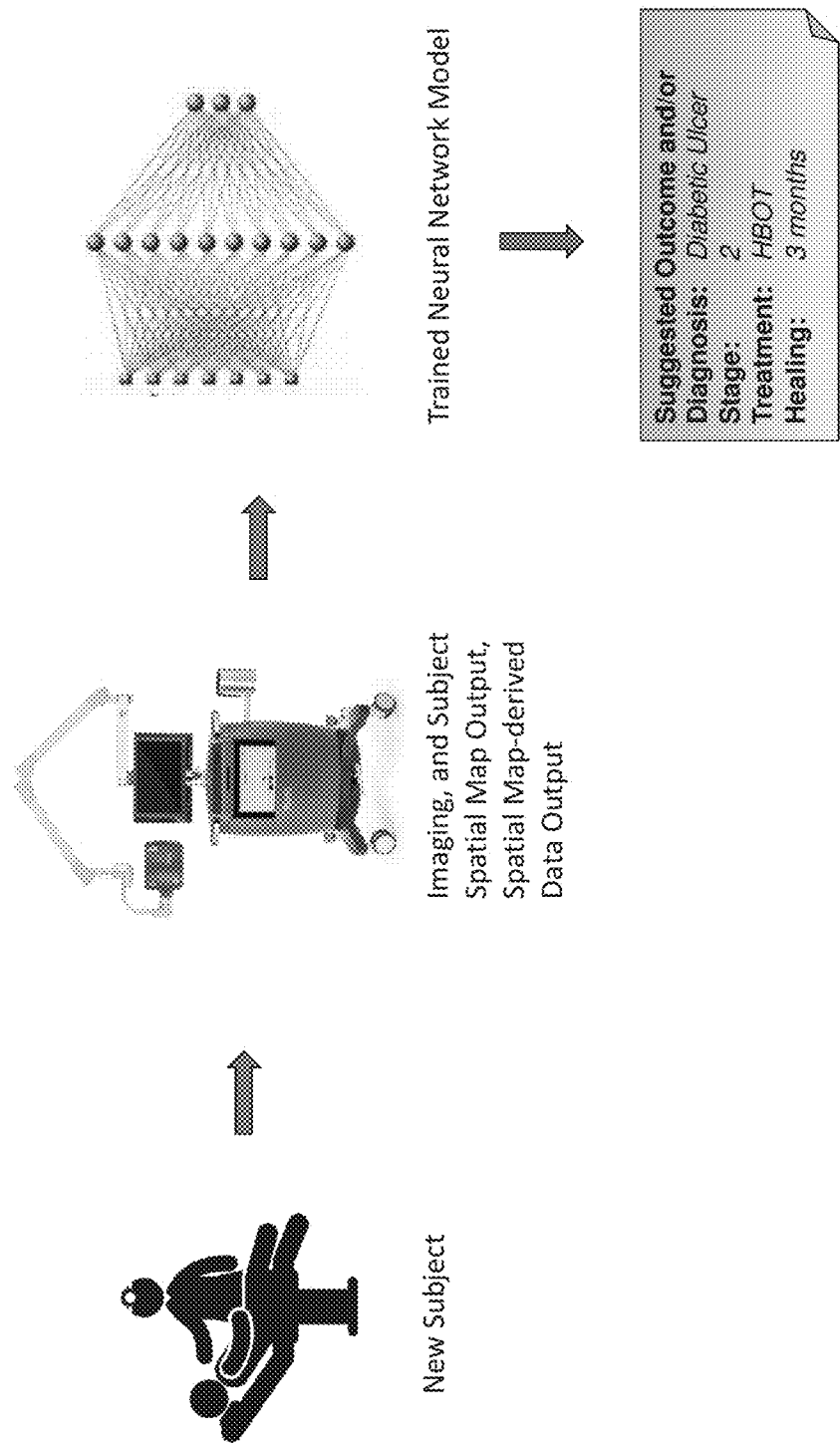
FIG. 5C is an illustrative diagram of using the methods and systems described herein in new data classification for predicting clinical data and/or diagnosis.

In some variations, as is illustrated in the example method 500 in FIG. 5A, the method may be used for predicting clinical data. The method 500 may comprise receiving data for a subject time series of fluorescence images of the subject 510 which may be generated and processed as described in connection with the various variations above, and using the predictive model 512 generated according to the methods described above for predicting clinical data associated with the subject time series of fluorescence images of the subject 514. FIG. 5B illustrates, graphically, use of the spatial map generated according to the various methods described herein in combination with subject metadata for generation of a database or registry, and further for generation of a neural network classification model. Thus, as is illustrated schematically in FIG. 5C, a new subject may be evaluated by generating the subject time series of fluorescence images of the tissue under evaluation during imaging, generating the subject spatial maps as was described herein, storing such map in a database or registry, storing various data derived from the map (e.g., statistical data derived from the map such as, for example, percentage of each cluster in the map, their mean/median/standard deviation, map histogram or a combination thereof), one or more of which may then be used as input into the previously generated/trained classification neural network model, which in turn would suggest a possible predicative outcome (e.g., diagnosis) for considering by the clinician and to help facilitate diagnosis by the clinician. In various embodiments, such a system would not provide a diagnosis but rather a potential suggested outcome, in other variations, such a system would provide a diagnosis. In various other variations, such a system would not be used for facilitating a diagnosis but rather for building a database or registry of spatial maps, data derived from the spatial maps, or a combination thereof. The database or registry, may for example, comprise such data organized by tissue type, modality, clinical conditions, which when accessed by a user (e.g., a clinician) may help facilitate a diagnosis.

Thus, in some variations, as is illustrated in the example method 600 in FIG. 6, the method for characterizing tissue of a subject may comprise receiving data for a plurality of time series of fluorescence images 612, selecting a feature vector for the data, each feature vector characterizing one or more features of the data 614, generating a dataset comprising the feature vectors 616, categorizing the dataset to generate a labeled dataset 618, and generating a plurality of centroids 620. In some variations, the output centroids may be further used for building spatial (cluster) maps for new subject data as was described above. In further variations of the method for characterizing tissue of a subject may comprise receiving a training dataset comprising a plurality of feature vectors characterizing one or more features of a plurality of data entries, wherein each data entry is at least a portion of a time-intensity curve for a training subregion in a training time series of fluorescence images.

In some variations, the tissue may include, for example, healthy tissue, unhealthy tissue, wound tissue or a combination thereof. The wound may include any kind of chronic or acute injury to tissue, such as an incision, a pressure ulcer, a venous ulcer, an arterial ulcer, a diabetic lower extremity ulcer, a laceration, an abrasion, a puncture, a contusion, an avulsion, a cavity, a burn, a combination thereof, and/or the like. Furthermore, the wound may be caused by one or more of various trauma events and/or medical conditions, such crush wounds, battle wounds (e.g., gunshot/explosion), or wounds resulting from gangrene, inflammation, venous stasis, lymphedema, etc.

One challenge in wound management is that the medical condition or nature of a wound can be viewed differently among clinicians depending, for example, on the skill and experience of the clinician. Conventionally, wound management techniques may provide information about the wound's pathological history, but fail to provide reliable indicators of viability and/or restorative potential (e.g., whether wound and/or periwound is likely to develop complications, is capable of healing, how healing progresses, and whether the treatment applied is effective and when it can be discontinued). Furthermore, wounds exist where no pathology is demonstrable by conventional techniques.

Conventionally, in an attempt to address some of these challenges, some fluorescence imaging technology may, in addition to providing a visual display, generate metrics from the video data in order to numerically characterize the blood flow and/or perfusion in and around the wound, and thereby attempt to reduce subjectivity and perception biases in assessing the tissue blood flow and/or perfusion status. However, such a numeric characterization is not informed by an understanding of the underlying biological mechanisms of wound healing, which is necessary in order to convey information which would allow clinicians to make clinically meaningful assessments. More specifically, a comprehensive understanding of blood flow and/or tissue perfusion dynamics during the wound healing process would be helpful for such image data to yield an accurate interpretation of wound healing status. Existing fluorescence imaging technologies do not incorporate such knowledge and subsequently fail to support a standardized protocol for assessing blood flow and/or tissue perfusion, and fail to provide accurate characterization and classification of blood flow/perfusion behavior in the tissue that is sufficiently consistent between clinicians, between patients, and between multiple imaging sessions.

In one variation, the methods described herein relate to medical imaging technology for characterizing a wound in a target tissue region (e.g., wound, periwound). The spatial maps and/or subject spatial maps (cluster maps) generated using the methods described herein demonstrate both simplicity of interpretation and overall accuracy with respect to characterizing the tissue, which stem from the quality of the measured signals rather than subjective human selection of relevant parameters. The methods may provide enhanced diagnostic power by minimizing any dilution of the information of interest. Moreover, the methods may provide a consistent objective representation of the state of the target tissue (e.g., wound or periwound) that is not subject to biases of perception and/or skill of a clinician. Furthermore, the methods may provide a reliable and consistent way to compare and track wound healing status (e.g., based on blood flow and/or perfusion) of a subject over time across multiple imaging sessions. Thus, the methods may enable a more accurate and consistent assessment of the target tissue region, as well as targeted formulation of clinical care strategies (e.g., recommending treatments, monitoring of treatment efficacy, determining if/when the treatment should be discontinued, formulating surgical strategy). Ultimately, the methods may also may facilitate decreasing patient risk for patients who are sensitive to medication, and decreasing the total cost of procedure and/or treatment.

Assessing a wound according to the various embodiments encompasses the assessment of perfusion dynamics. For example, the methods and systems described herein are applicable to other clinical applications such as, for example, pre-surgical evaluation of patients undergoing plastic reconstruction procedures, general surgical procedures involving tissue reapproximation with vascular anastomoses (e.g., skin flap transfers, colon reconstruction, etc.) or assessment of viability and function of cardiac tissue during cardiac surgery. Furthermore, the methods and systems described herein are further applicable to a clinical evaluation of any dynamic process, such as for example tissue perfusion or other dynamic behavior of an imaging agent in tissue, that can be represented by a spatial map of image data generated from a time series of input data (e.g., image frames) that exhibit the process.

The data derived from performing the method and using the systems described herein yet further facilitates distinguishing between multiple wound regions in the target tissue which may develop, progress and/or heal according to different time lines.

Additionally, although variations of the method are described herein in the context of a time series of fluorescence images, the method may be applied to other sources of input data generated as a time series which relate to a dynamic behavior of an imaging agent in the tissue and for other clinical purposes where the target tissue comprises regions with differing tissue properties. Examples can include detection of fluorescence from an excited imaging agent, as well as other sources of input data, such as a time series of images generated by detection of absorption associated with an imaging agent.

Quantification of the Clusters, the Spatial Map, the Subject Spatial Map or a Combination Thereof The methods of the present invention may further comprise quantification of the classified clusters, the spatial map generated from the clusters, the subject spatial map generated from the subject time series of fluorescence images or a combination thereof. The quantification may involve generating a numerical value (a quantifier) for the regions of interest in the maps or for the entire map.

The generated numerical value may provide a quantitative representation of the tissue (e.g., wound). According to an embodiment, the numerical value may represent tissue activity (e.g., a wound activity value). The numerical value may be tracked over time, which may be represented in a graph form which facilitates deriving information about the rate and slope. A graph representation of the numerical value over time may facilitate an evaluation of a change in the numerical value over time, which in some embodiments may be indicative of a change in a state or activity of the tissue (e.g., wound) over time. Examples of the state or activity of the tissue include a property of the tissue, a condition of the tissue, healing status of the tissue (e.g., inflammation, malignancy, abnormality, disease). Tracking the numerical value over time facilitates tracking the rate of change which, for example, may be correlated with the stages of the tissue healing (e.g., wound healing). Tracking the numerical value over time may further be correlated with the angiogenesis and the stage of healing the patient is in. Furthermore, information relating to a change in the numerical value over time may provide predictive information regarding the point at which a treatment, such as hyperbaric oxygen therapy, negative pressure therapy, or other known wound care therapies, may be stopped without compromising the healing process. As a result, the numerical value may provide for an objective, standardized protocol for assessing tissue blood flow and/or tissue perfusion, which may facilitate a way to reliably and consistently compare and track blood flow and/or perfusion status of a subject over time across multiple imaging sessions, regardless of the clinician performing the assessment. In some variations, the numerical value (quantifier) itself may be complex when it is derived from, for example, various kinds of categories of curves present in the spatial map and/or statistics relating to the distribution of clusters in the spatial map, or other parameters.

In some variations, the methods may further include displaying the numerical value (quantifier) on a display. For example, the numerical value may be displayed within a user interface on a video monitor in a fluorescence imaging system, or other suitable display. In some variations, the numerical value can be used alone or in combination with a visualization of the other steps of the methods described herein to enhance the information conveyed to the clinician (which facilitates enhanced diagnostics), which may further be overlaid over an anatomical image and/or correlated with other data or information regarding the subject (e.g., a systemic condition of the patient). For example, in some variations, the numerical value may be displayed alone or in combination with the subject spatial map (e.g., 122, 422). As another example, the numerical value may be displayed in combination with a spatial (cluster) map and/or other suitable maps or images. In some variations, the numerical value may be correlated with a risk estimate for clinically relevant (e.g., perfusion-related) condition. Such assessments may be made pre-intervention, during treatment/procedure, and/or post-intervention. The methods may also further comprise defining a diagnosis to identify and characterize a clinically relevant (e.g., perfusion-related) condition in the subject pre-intervention, during treatment/procedure, and post-intervention. In various other embodiments, the method may exclude the correlation and/or diagnoses steps.

The various aspects of the methods are further illustrated in the Examples section with application to various clinical contexts.

Systems for Characterizing Tissue and/or Predicting Clinical Data

A system for characterizing tissue of a subject and/or predicting clinical data and/or outcomes, according to some variations, includes an imaging system for acquiring a time series of images of tissue (e.g., a time series of fluorescence images), and one or more processors and memory having instructions stored thereon, wherein the instructions when executed by the one or more processors cause the system to perform the methods substantially as described above for characterizing tissue and/or predicting the clinical data.

Figure 7:
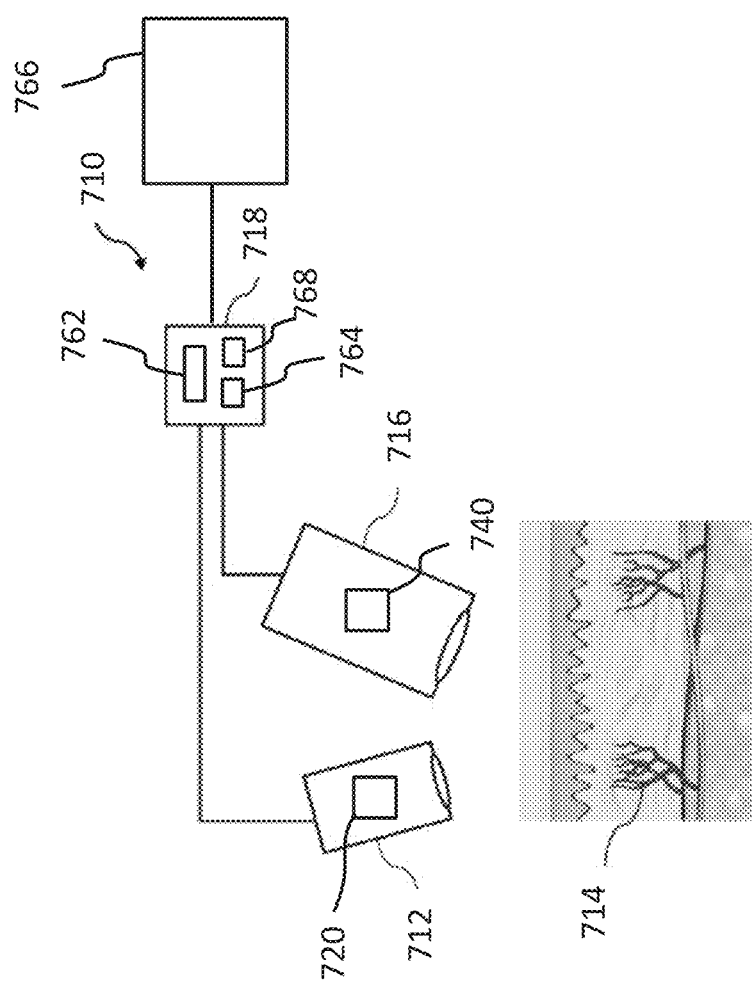
FIG. 7 is an illustrative depiction of an exemplary fluorescence imaging system arranged for characterizing tissue of a subject.

In some variations, the system for generating a time series/subject time series of fluorescence images, and/or characterizing tissue of a subject and/or predicting the clinical data as described herein in connection with the various variations is a fluorescence imaging system. FIG. 7 is a schematic example of a fluorescence imaging system 710. The fluorescence imaging system 710 comprises a light source 712 to illuminate the tissue of the subject to induce fluorescence emission from a fluorescence imaging agent 714 in the tissue of the subject (e.g., in blood), an image acquisition assembly 716 arranged for generating the time series and/or the subject time series of fluorescence images from the fluorescence emission, and a processor assembly 718 arranged for processing the generated time series/subject time series of fluorescence images according to any of the variations of the methods described herein. The processor assembly 718 may include memory 768 with instructions thereon, a processor module 762 arranged for executing the instructions on memory 768 to process the time series and/or subject time series of fluorescence images as described herein in connection with the various embodiments of the methods, and a data storage module 764 to store the unprocessed and/or processed time series and/or subject time series of fluorescence images. In some variations, the memory 768 and data storage module 764 may be embodied in the same storage medium, while in other variations the memory 768 and the data storage module 764 may be embodied in different storage mediums. The system may further include a display 766 on which to display images and other data, such as some or all of the time series/subject time series of fluorescence images or other input data, spatial maps, subject spatial maps, and/or a tissue numerical value (quantifier).

Figure 8:
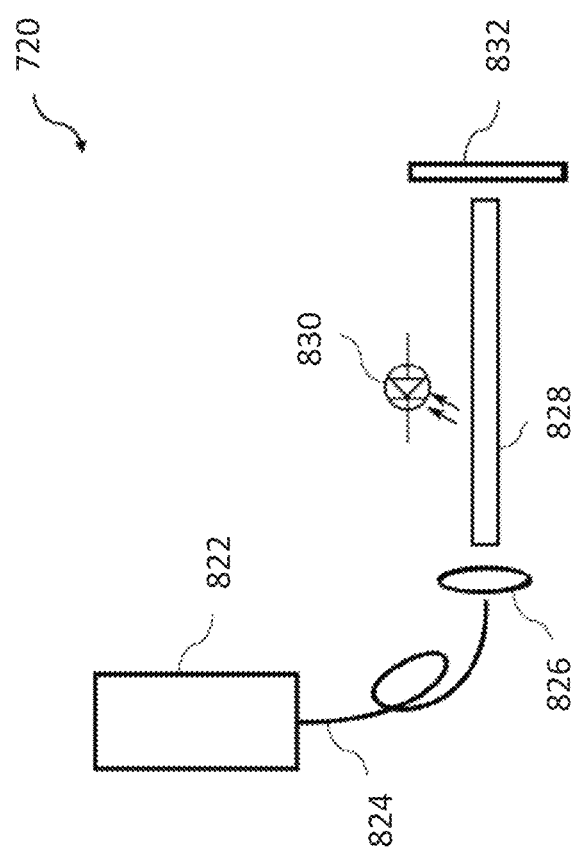
FIG. 8 is an illustrative depiction of an exemplary illumination module of a fluorescence imaging system arranged for characterizing tissue of a subject.

In some variations, the light source 712 includes, for example, an illumination module 720. Illumination module 720 may include a fluorescence excitation source arranged for generating an excitation light having a suitable intensity and a suitable wavelength for exciting the fluorescence imaging agent 714. As shown in FIG. 8, the illumination module 720 may comprise a laser diode 822 (e.g., which may comprise, for example, one or more fiber-coupled diode lasers) arranged for providing an excitation light to excite the fluorescence imaging agent (not shown) in tissue of the subject. Examples of other sources of the excitation light which may be used in various embodiments include one or more LEDs, arc lamps, or other illuminant technologies of sufficient intensity and appropriate wavelength to excite the fluorescence imaging agent in the tissue. For example, excitation of the fluorescence imaging agent in blood, wherein the fluorescence imaging agent is a fluorescence dye with near infra-red excitation and emission characteristics, may be performed using one or more 793 nm, conduction-cooled, single bar, fiber-coupled laser diode modules from DILAS Diode Laser Co, Germany.

Referring again to FIG. 7, in some variations, the light output from the light source 712 may be projected through one or more optical elements to shape and guide the output being used to illuminate the tissue area of interest. The optical elements may include one or more lenses, light guides, and/or diffractive elements so as to ensure a flat field over substantially the entire field of view of the image acquisition assembly 716. The fluorescence excitation source may be selected to emit at a wavelength close to the absorption maximum of the fluorescence imaging agent 714 (e.g., ICG, etc.). For example, as shown in FIG. 8, the output 824 from the laser diode 822 may be passed through one or more focusing lenses 826, and then through a homogenizing light pipe 828 such as, for example, light pipes commonly available from Newport Corporation, USA. Finally, the light may be passed through an optical diffractive element 832 (i.e., one or more optical diffusers) such as, for example, ground glass diffractive elements also available from Newport Corporation, USA. Power to the laser diode 822 may be provided by, for example, a high-current laser driver such as those available from Lumina Power Inc. USA. The laser may optionally be operated in a pulsed mode during the image acquisition process. An optical sensor such as a solid state photodiode 830 may be incorporated into the illumination module 720 and may sample the illumination intensity produced by the illumination module 720 via scattered or diffuse reflections from the various optical elements. In some variations, additional illumination sources may be used to provide guidance when aligning and positioning the module over the area of interest.

Figure 9:
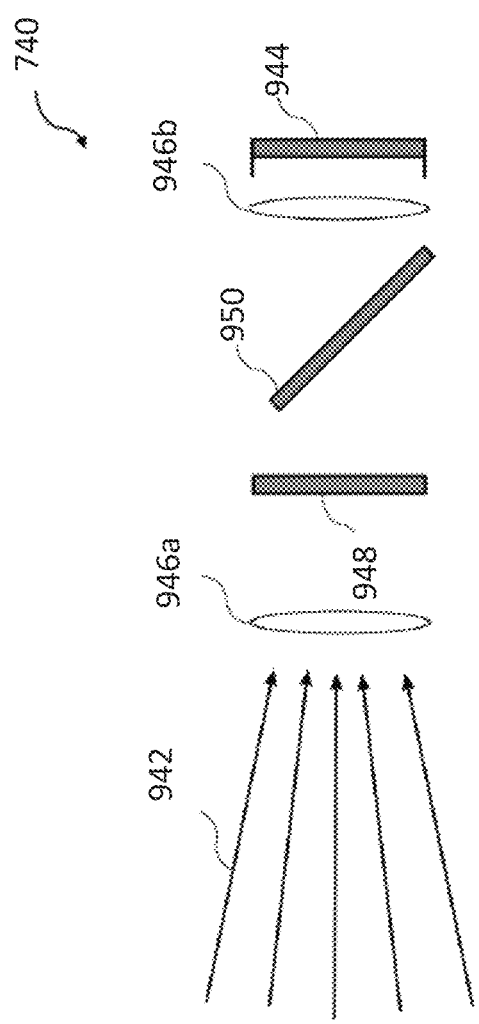
FIG. 9 is an exemplary camera module of a fluorescence imaging system arranged for characterizing tissue of a subject.

Referring again to FIG. 7, in some variations, the image acquisition assembly 716 may be a component of a fluorescence imaging system 710 configured to acquire the time series and/or subject time series of fluorescence images from the fluorescence emission from the fluorescence imaging agent 714. The image acquisition assembly 716 may include a camera module 740. As shown in FIG. 9, the camera module 740 may acquire images of the fluorescence emission 942 from the fluorescence imaging agent in the tissue by using a system of imaging optics (e.g., 946a, 946b, 948 and 950) to collect and focus the fluorescence emission onto an image sensor assembly 944. The image sensor assembly 944 may comprise at least one 2D solid state image sensor. The solid state image sensor may be a charge coupled device (CCD), a CMOS sensor, a CID or similar 2D sensor technology. The charge that results from the optical signal transduced by the image sensor assembly 944 is converted to an electrical video signal, which includes both digital and analog video signals, by the appropriate read-out and amplification electronics in the camera module 940.

According to an exemplary variation of a fluorescent imaging system, the light source may provide an excitation wavelength of about 800 nm +/−10 nm, and the image acquisition assembly uses emission wavelengths of >820 nm with NIR-compatible optics for, for example, ICG fluorescence imaging. In an exemplary embodiment, the NIR-compatible optics may include a CCD monochrome image sensor having a GigE standard interface and a lens that is compatible with the sensor with respect to optical format and mount format (e.g., C/CS mount).

In some variations, the processor module 762 comprises any computer or computing means such as, for example, a tablet, laptop, desktop, networked computer, or dedicated standalone microprocessor. For instance, the processor module 762 may include one or more central processing units (CPU). In an exemplary embodiment, the processor module 762 is a quad-core, 2.5 GHz processor with four CPUs where each CPU is a microprocessor such as a 64-bit microprocessor (e.g., marketed as INTEL Core i3, i5, or i7, or in the AMD Core FX series). However, in other embodiments, the processor module 762 may be any suitable processor with any suitable number of CPUs and/or other suitable clock speed.

Inputs for the processor module 762 may be taken, for example, from the image sensor 944 of the camera module 740 shown in FIG. 9, from the solid state photodiode 830 in the illumination module 720 in FIG. 8, and/or from any external control hardware such as a footswitch or remote-control. Output is provided to the laser diode driver and optical alignment aids. As shown in FIG. 7, in some variations, the processor assembly 718 may have a data storage module 764 with the capability to save the time series/ subject time series of images, or data representative thereof, or other input data to a tangible non-transitory computer readable medium such as, for example, internal memory (e.g. a hard disk or flash memory), so as to enable recording and processing of acquired data. In some variations, the processor module 762 may have an internal clock to enable control of the various elements and ensure correct timing of illumination and sensor shutters. In some variations, the processor module 762 may also provide user input and graphical display of outputs. The fluorescence imaging system may optionally be configured with a video display 766 or other monitor to display the time series of fluorescence images as they are being acquired or played back after recording. The video display 766 may additionally or alternatively visualize data generated during performance of the methods described herein, such as a spatial map, a subject spatial map, and/or tissue numerical value.

In operation of the exemplary system described in FIGS. 7-9, the subject is positioned relative to fluorescence imaging system 710 such that an area of interest (e.g., target tissue region) is located beneath the light source 712 and the image acquisition assembly 716 such that the illumination module 720 of light source 712 produces a substantially uniform field of illumination across substantially the entire area of interest. In some variations, prior to the administration of the fluorescence imaging agent 714 to the subject, an image may be acquired of the area of interest for the purposes of background deduction. To acquire fluorescence images/subject fluorescence images, the operator of the fluorescence imaging system 710 may initiate the acquisition of the time series/subject time series of fluorescence images by depressing a remote switch or foot-control, or via a keyboard (not shown) connected to the processor assembly 718. As a result, the light source 712 is turned on and the processor assembly 718 begins recording the fluorescence image data/subject fluorescence image data provided by the image acquisition assembly 716. When operating in the pulsed mode of the embodiment, the image sensor 944 in the camera module 740 is synchronized to collect fluorescence emission following the laser pulse produced by the diode laser 822 in the illumination module 720. In this way, maximum fluorescence emission intensity is recorded, and signal-to-noise ratio is optimized. In this embodiment, the fluorescence imaging agent 714 is administered to the subject and delivered to the area of interest via arterial flow. Acquisition of the time series/subject time series of fluorescence images is initiated, for example, shortly after administration of the fluorescence imaging agent 714, and the time series of fluorescence images from substantially the entire area of interest is acquired throughout the ingress of the fluorescence imaging agent 714. The fluorescence emission from the region of interest is collected by the collection optics of the camera module 740. Residual ambient and reflected excitation light is attenuated by subsequent optical elements (e.g., optical element 950 in FIG. 9 which may be a filter) in the camera module 740 so that the fluorescence emission can be acquired by the image sensor assembly 944 with minimal interference by light from other sources.

In some variations, following the acquisition or generation of the time series/subject time series of fluorescence images, the processor assembly 718 (e.g., processor module 762 or other processor) may then be initiated to execute instructions stored on memory 768 and perform one or more methods as described herein. The system 710 may visualize on display 766 the spatial map/subject spatial map and/or any clinical correlations or diagnosis derived therefrom or both may be displayed to the user as, for example, a grayscale or false color image, and/or stored for subsequent use. Additionally or alternatively, the system 710 may display on display 766 a tissue numerical value.

In some variations, the system for characterizing tissue or predicting a clinical data and/or outcomes comprises a user interface, a processor arranged for communicating with the user interface, and a non-transitory computer-readable storage medium having instructions stored which, when executed by the processor, cause the processor to perform one or more of the methods for characterizing tissue and/or predicting a clinical data described herein. In some variations, the processor may be a component of the imaging system. In other variations, the processor may be located remotely from and in communication with an imaging system, where the imaging system may be the fluorescence imaging system described above, or any suitable imaging system.

A tangible non-transitory computer readable medium having computer-executable (readable) program code embedded thereon may provide instructions for causing one or more processors to, when executing the instructions, perform one or more of the methods for characterizing tissue and/or predicting clinical data described herein. Program code can be written in any appropriate programming language and delivered to the processor in many forms, including, for example, but not limited to information permanently stored on non-writeable storage media (e.g., read-only memory devices such as ROMs, CD-ROM disks, etc.), information alterably stored on writeable storage media (e.g., hard drives or the like), information conveyed to the processor through communication media, such as a local area network, a public network such as the Internet, or any type of media suitable for storing electronic instruction. When carrying computer readable instructions that implement the various embodiments of the method of the present invention, such computer readable media represent examples of various embodiments of the present invention. In various embodiments, the tangible non-transitory computer readable medium comprises all computer-readable media, and the present invention scope is limited to computer readable media wherein the media is both tangible and non-transitory.

A kit may include any part of the systems described herein and the fluorescence imaging agent such as, for example, a fluorescence dye such as ICG or any suitable fluorescence imaging agent. In further aspects, a kit may include a tangible non-transitory computer readable medium having computer-executable (readable) program code embedded thereon that may provide instructions for causing one or more processors, when executing the instructions, to perform one or more of the methods for characterizing tissue and/or predicting clinical data described herein. The kit may include instructions for use of at least some of its components (e.g., for using the fluorescence imaging agent, for installing the computer-executable (readable) program code with instructions embedded thereon, etc.). In yet further aspects, there is provided a fluorescence imaging agent such as, for example, a fluorescence dye for use in in the methods and systems described herein. In further variations, a kit may include any part of or the entire system described herein and a fluorescence agent such as, for example, a fluorescence dye such as ICG, or any other suitable fluorescence agent, or a combination of fluorescence agents.

EXAMPLES

Application of the Methods and Systems in Wound Management

One challenge in wound management, such as chronic wound management, is that the medical condition or nature of a wound can be viewed differently among clinicians. Conventional techniques may provide information about the wound's pathological history, but fail to provide reliable indicators of viability and/or restorative potential, e.g., whether wound and/or periwound is likely to develop complications, is capable of healing, or how healing progresses (e.g., time to achieve an acceptable healing stage). Furthermore, wounds exist where no pathology is demonstrable by conventional diagnostic techniques. Various embodiments of the methods and systems described herein facilitate producing a consistent representation (not subjective to biases of perception) of the state of a particular tissue region (e.g., wound, periwound), and thus facilitate a more accurate subsequent assessment and formulation of care strategies (e.g., recommendation and assessment of efficacy care such as, for example, topical treatments, hyperbaric therapy; assessment of the tissue pre- and post-surgery; formulation of surgical strategy, recommendations relating to the period of time to achieve various stages of healing of the tissue).

Training Set 1—Breast Tissue in Reconstructive Surgery

Figure 10:
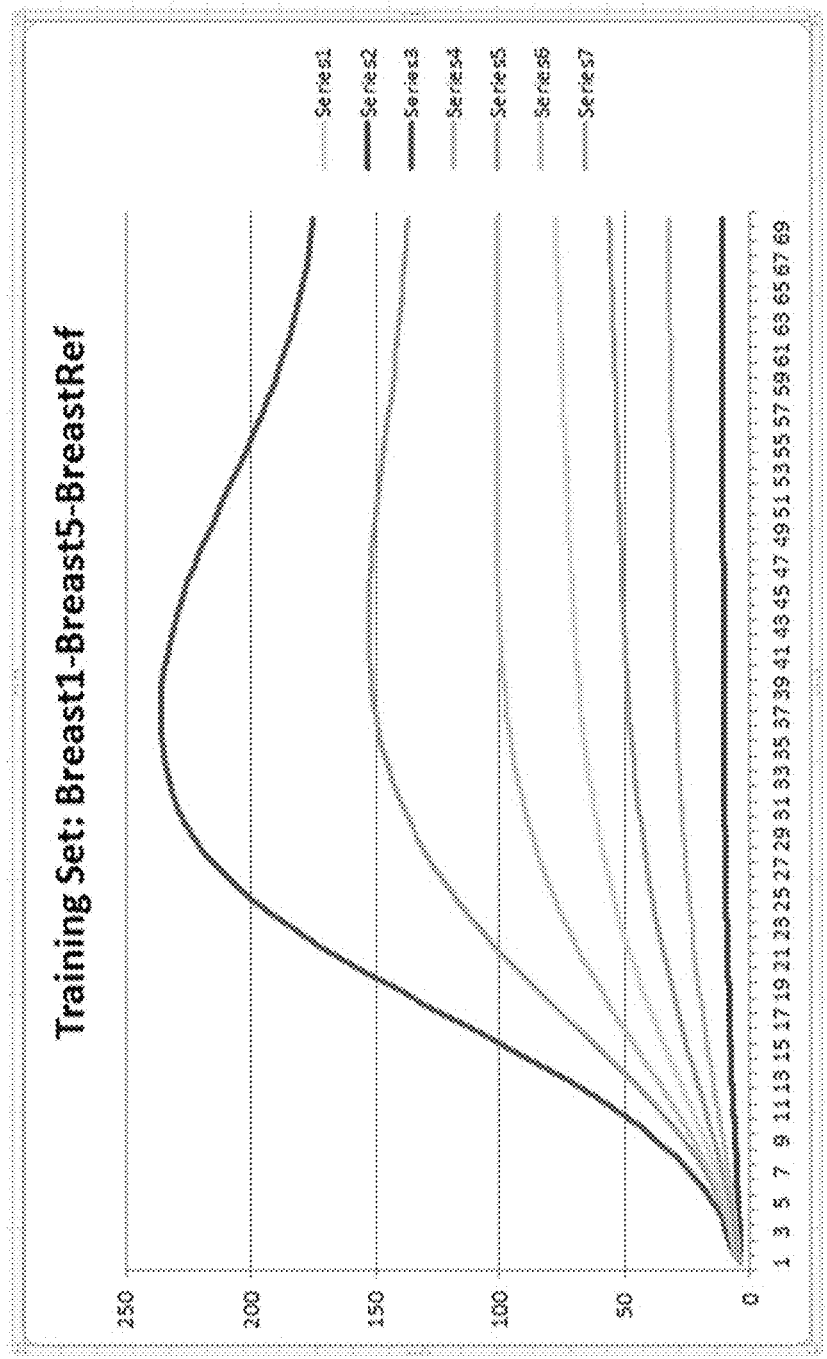
FIG. 10 illustrates the centroids generated for breast tissue.

FIGS. 10 and 11 illustrate an application of the methods and systems according to various embodiments to reconstructive breast surgery. Data was collected in the course of mastectomy surgery. The patient was a 46 year old female who underwent bilateral mastectomies with immediate reconstruction. 48 hours postoperatively, she was deemed to have ischemic compromise of the inferior pole of the right breast. HBOT therapy was recommended. A time series of fluorescence angiography images (videos) were recorded with the aid of SPY® Elite fluorescence imaging system (available from NOVADAQ® Technologies Inc.). Three types of recordings were performed for each breast undergoing treatment: pre-incision baseline, post-mastectomy, and post-reconstruction. In addition, a color snapshot was taken a week after the procedures as means to evaluate the clinical outcome.

The first dataset as described in connection with the methods and systems according to various embodiments was created by combining pixel intensity curves for three different sequences of the breast. K-means algorithm was then trained on this dataset to generate the model with seven centroids, which are illustrated in FIG. 10.

Two of the training sequences and one new sequence were subsequently labeled by applying this trained model to their pixels. As a final step, a visual spatial map was generated for the three sequences by assigning each pixel the color corresponding to the color of its associated centroid (shown on the legend of the centroid graphs in FIG. 10). FIGS. 11A, 11B and 11C are color images of the wound during an initial assessment (FIG. 11A) and thereafter following treatment which were taken at 1 week (FIG. 11B) and 3 weeks (FIG. 11C) after the initial assessment. FIGS. 11D, 11E, and 11F are the corresponding spatial (cluster) maps generated according to the methods and systems described herein.

This case demonstrates the healing of a hypo-perfused wound. As is illustrated in FIGS. 11D, 11E and 11F, the spatial (cluster) maps provide details about the blood flow and/or perfusion that are not evident from visual-light images in FIGS. 11A, 11B and 11C. The spatial (cluster) map images have identified an area (indicated with an arrow) adjacent the nipple in which the tissue was significantly different (compromised) as compared to the neighboring tissue.

HBOT therapy has triggered the process of angiogenesis that resulted first in increased blood flow activity around the hypo-perfused area of the tissue (FIG. 11D, arrow). As the healing progresses, the increased flow spreads inside the wound as evidenced by collapse of the dark blue region with time and increased blood flow and/or perfusion (FIGS. 11E, 11F). The healing progression is evidenced in the spatial (cluster) maps by how the intensity curves gradually change from the centre of the wound outward, namely from dark blue to sky blue to green to yellow, with the dark blue region eventually collapsing as the healing progresses. The spatial (cluster) maps indicate that the healing does not happen abruptly, but rather graduallly and symetrically around the wound. Such information would not have been apparent from the examination of the color images (i.e., FIGS. 11A, 11B, and 11C).

Training Set 2—Foot

A time series of fluorescence angiography images (videos) were recorded with the aid of LUNA® fluorescence imaging system (available from NOVADAQ® Technologies Inc.). The time series of fluorescence images of the foot and the foot dataset were generated in a manner similar to the example relating to breast tissue. More specifically, the foot dataset was created by combining the pixel intensity data over time from three different sequences of a foot, then trained using seven clusters and the K-means algorithm. The resulting centroids are shown in FIG. 12A, and the generated spatial maps illustrating the status of the wound are illustrated in FIGS. 12B and 12C.

Application of Cluster Analysis in Generation of Universal Perfusion-Based Wound Scale for Tissue Classification There are many existing wound classification systems including, for example, (i) the Wagner classification for neuropathic ulcers, which grades the wound by its depth and the presence of infection, and has 5 numeric grades;

(ii) the University of Texas Scheme also used for neuropathic ulcers, which grades the wound by its depth and the presence of infection, and has 4 numeric grades for depth and 4 letter grades for infection and ischemia;

(iii) National Pressure Ulcer Advisory Panel Classification, which grades pressure ulcers by its color, tissue loss and presence of slough, and defines 6 numeric stages;

(iv) the Rutherford and the Fontaine Scheme used for arterial insufficiency ulcers which grades the wound by its clinical presentation, and has 4-6 descriptive stages;

(v) the CEAP classification for venous insufficiency ulcers which consists of two parts that are scored separately, and has 4 letter grades for Part I and 3 numeric grades for Part II.

There is also a special grading system for burn injuries (which ranks the wounds by their depths and affected area), as well as the PEDIS System, the DEPA score, and the SAD score for diabetic foot ulcers.

The existent wound classification systems are mainly based on grading the surface appearance of the wound, as well as its texture and morphology. As a result, different systems have evolved for different wound etiologies in order to efficiently capture the wide spectrum of compromised tissue variations So many options available to clinicians raise the issues as to which system should the clinicians use. Having several different systems for description of similar types of wounds has obvious disadvantages, therefore a well-designed universal wound classification scheme would be advantageous.

The methods and systems described herein may facilitate identifying unique blood flow patterns and correlating them with the respective types of wounds, thus creating a universal wound classification system based on the underlying perfusion profile and can be applied to different wound etiologies and severities. The wound grade based on such a scale can be correlated with its etiology, healing potential and optimal treatments.

A number of patients (~20) undergoing treatments for a variety of chronic wounds (DFU-s, trauma, surgery, arterial ulcers) were imaged weekly with the aid of LUNA® imaging system (available from Novadaq Technologies® Inc.) for 5 consecutive weeks (on average). Maximum intensity maps have been generated from NIR video sequences recorded in the course of imaging sessions (a "maximum intensity map" refers to a map created by assigning each pixel in the calculation region of the time series of fluorescence input images the value of its maximum intensity reached during the entire measurement period), and wound resolution date has been noted by the attending physician at the end of patient's treatment. Subsequently, the time interval between the date of a particular imaging session and the wound resolution date has been calculated and associated with every maximum intensity map. In order to generate sufficient number of training and testing samples, the continuous labels representing healing time in days have been replaced by discrete categories of 'healing bins': "A"—time to healing from 0 to 20 days, "B"—time to healing from 21 to 80 days, and "C"—time to healing over 80 days. The resulting about 100 samples dataset comprised maximum intensity map images each labeled with associated 'healing bin' grade (A, B or C).

Figure 13:
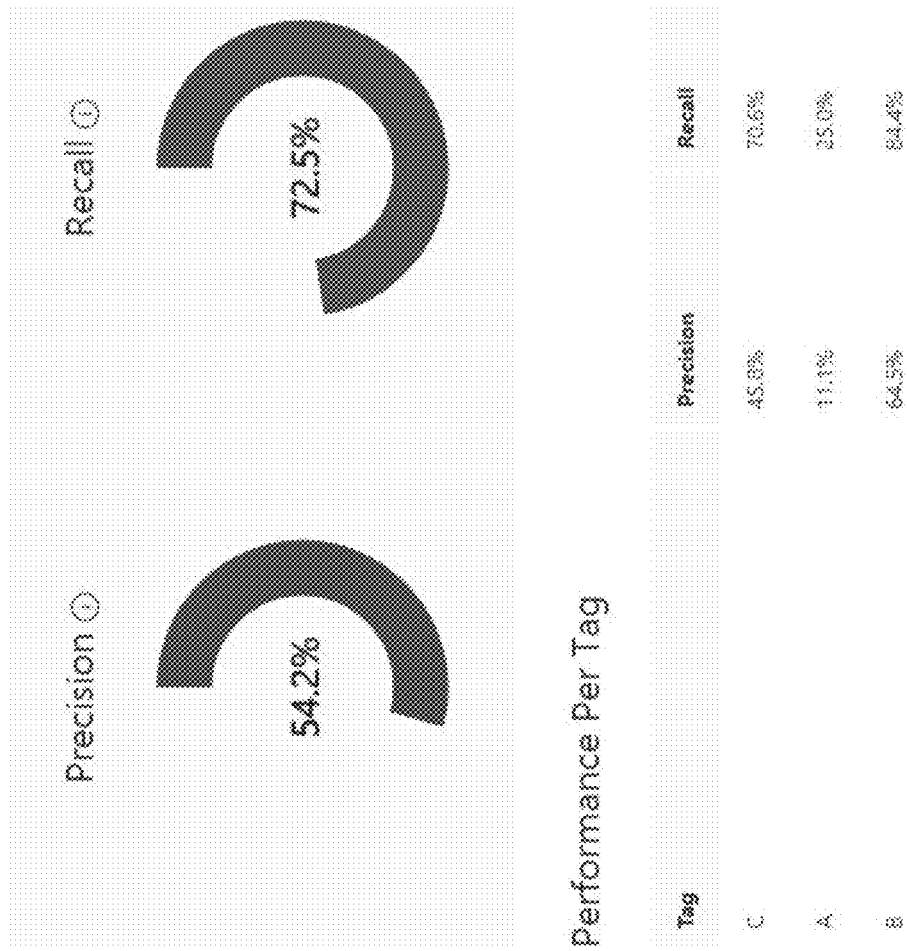
FIGS. 13 and 14 illustrate an exemplary training method according to an embodiment.

For this example, Microsoft Custom Vision cloud-based service (customvision.ai) was chosen as a training platform for the predictor. This tool allows building custom image classifiers with as few as 20-30 training images per category. To select the training samples, the following criteria were used: representative variety of imaged anatomy (i.e. foot, leg, heel, hand, abdomen), presence of noise in some images, and representative variety of wound etiologies (e.g. diabetic foot ulcer (DFU), trauma, surgery). Since the maps were generated using identical false-color scheme, the image classifier in this example required fewer training samples in order to identify the relevant blood flow patterns correlated with the healing times. In this example, the training procedure was performed in two iterations. First, a selected number of images (e.g., 76) of maximum intensity maps were uploaded to the cloud-based service and tagged with their respective 'healing grades': 11 A-s, 45 B-s, 20 C-s. After the training, the performance of the classifier has been automatically evaluated on the training set using k-fold cross validation, and precision/recall metrics were generated as a measure of the classifier's predicting abilities. As is illustrated in FIG. 13, the classifier performed the best in identifying Grade B, with the worst scores achieved for Grade A. These results are in direct correlation with the numbers of training samples for each category: highest for B-s, lowest for A-s. Additional tagged images were subsequently uploaded to the training platform (e.g., 10 additional images), so that the new training set comprised 86 images total: 13 A-s, 49 B-s, 24 C-s, and re-trained the classifier.

Figure 14:
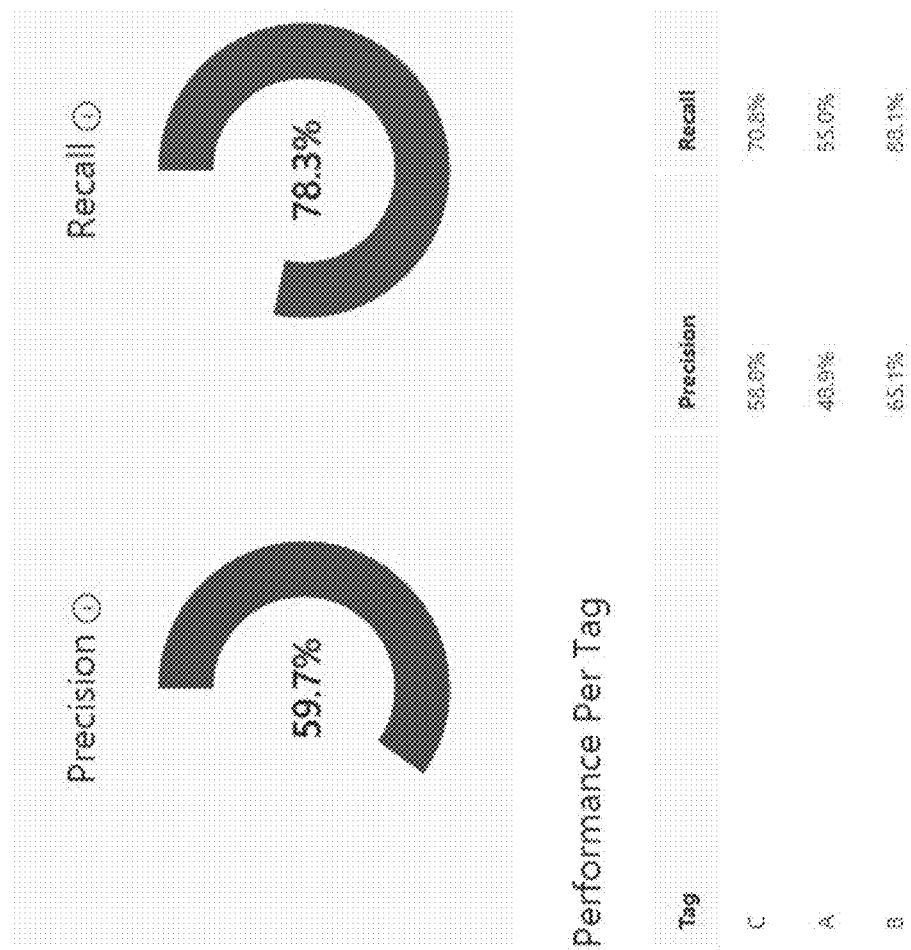

The evaluation results for the second iteration are shown in FIG. 14, which indicates an improvement in overall scores, with an especially significant change for Grade A predictions.

Figure 15:
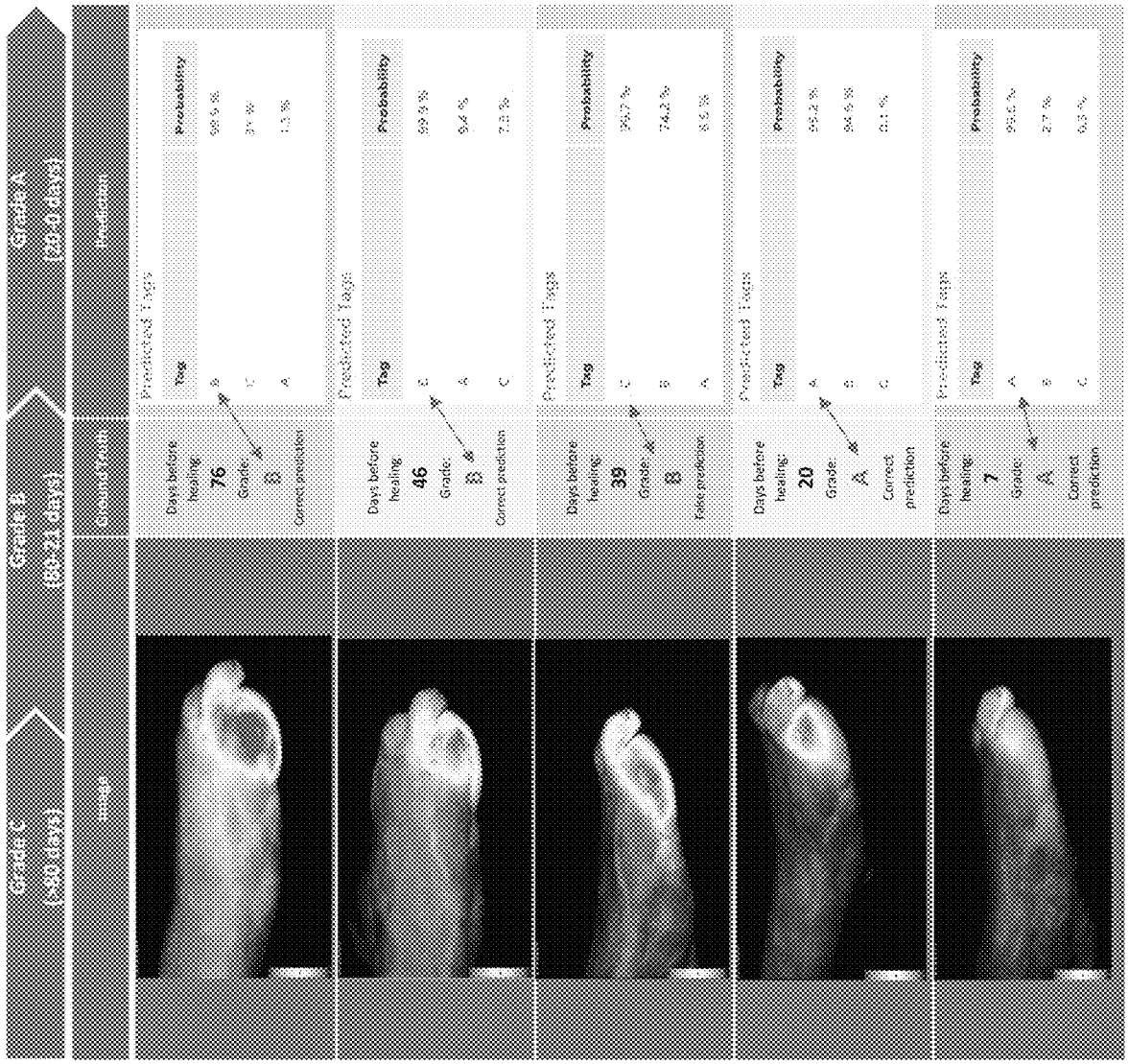
FIG. 15 illustrates an exemplary use of a neural network to predict clinical data (healing time) of a wound based on a model trained on fluorescence images of the wound/tissue as described in connection with FIGS. 13 and 14.

To test the trained classifier from Iteration 2 in FIG. 14, a set of 5 images from a single patient with known 'days before healing' metric associated with each image was used. These images were never 'seen' before by the classifier, thus allowing to measure how well it generalizes with regard to new data. FIG. 15 (presented along with the 'healing bins' scale) shows images submitted for predictions, the ground truth labels associated with the images, and the tags predicted by the classifier along with their probabilities. The ground truth labels predicted correctly are shown in green (labeled as "correct prediction"), while false predictions are shown in red (labeled as "false prediction"). As is illustrated by the results in FIG. 15, the classifier predicted correctly all labels but one. Furthermore, as is illustrated in FIG. 15, both the probability and the label of the second choice change consistently as the healing progresses along the timeline.

For example, the first sample in FIG. 15 is marked as being 76 days away from healing, which puts it in the B-bin (80-21 days) but very close to the boundary of the C-bin (>80 days). While the classifier has correctly predicted the most likely category as B, it has also assigned 31% probability of C-label.

The second sample (46 days from healing) in FIG. 15 is approximately in the middle of the B-category, which is correctly reflected by the classifier by assigning 99.9% to B-label and much lower but almost equal probabilities of being either A or C (9.4% and 7.3% respectively).

The third sample (39 days from healing) in FIG. 15 has been misclassified as C-grade, although it assigned relatively high probability to the correct grade of B as well (74.2%).

The fourth sample (20 days from healing) in FIG. 15 lies exactly at the division boundary between A and B categories, and the classifier correctly assigned equally high probabilities to both grades (95.2% for A and 94.6% for B).

Finally, the last sample in FIG. 15 shows the wound almost completely healed, and the classifier correctly assigned very high probability for grade A (99.6%) and very low probabilities for B and C (2.7% and 0.3% respectively).

The training and prediction trends as described herein indicate that increased number and variety of training samples, and introduction of more labels representing narrower time intervals, facilitate achieving higher accuracy and consistency of healing grade predictions on the new data.

Figure 16:
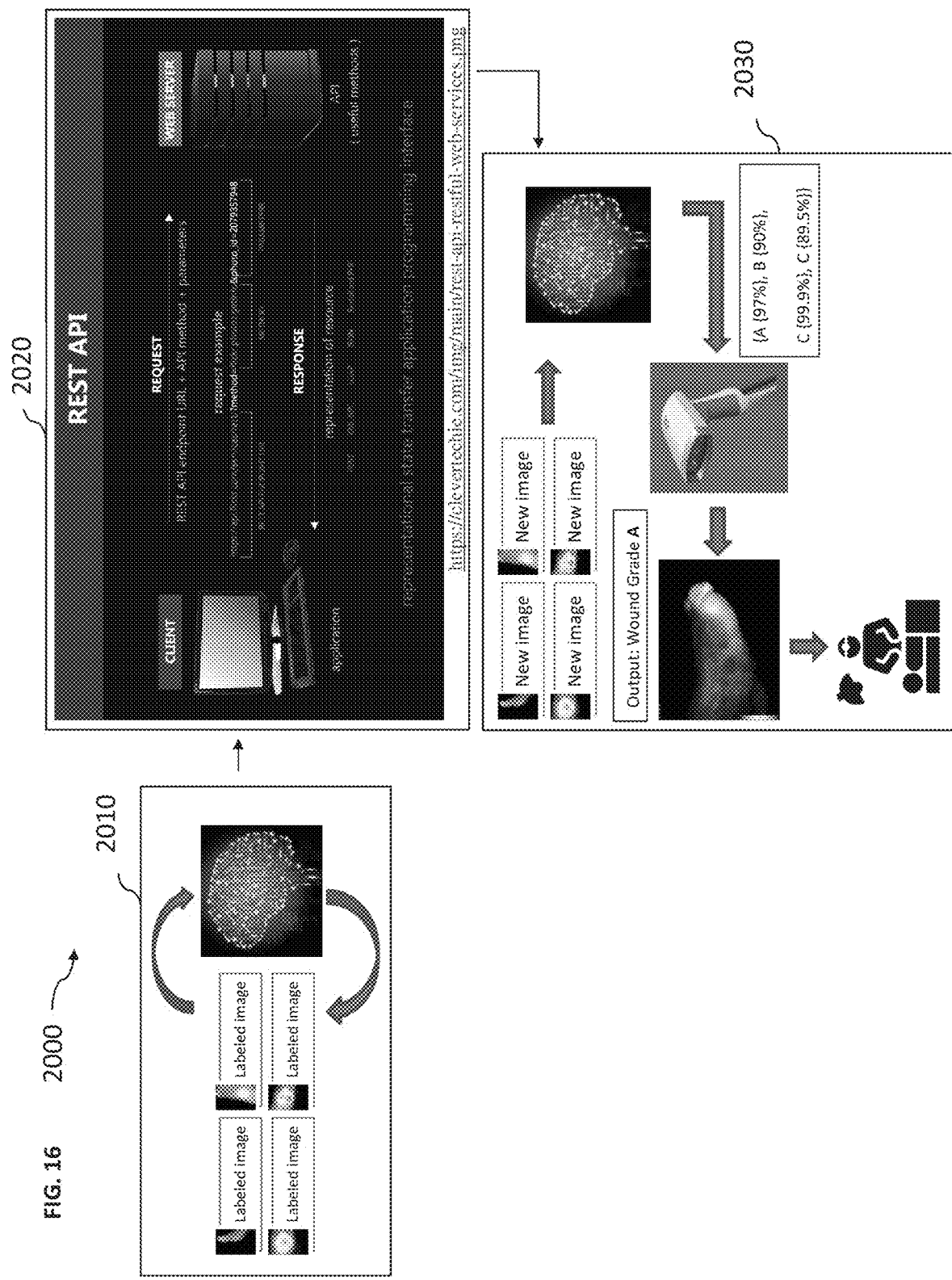
FIG. 16 schematically illustrates an example clinical application comprising training and predicting clinical data in accordance with the various embodiments herein.

FIG. 16 illustrates schematically an exemplary method 2000 for training the classifier on fluorescence image data, and using the trained classifier for predicting clinical data. As is shown in FIG. 16, a classifier may be trained using the Custom Vision cloud service 2010 described herein. Once the performance of the trained classifier reaches an acceptable level, the trained model may then be deployed as a REST API service 2020. Using a published URL for the prediction endpoint, a client application can submit REST API requests to the server to predict labels for new images and receive responses with the resulting tags 2030 as described herein in various embodiments. An output of a wound classification scale (wound grade) is generated based on automatically classifying, for example, perfusion patterns in tissue and assigning clinical observations correlated with a particular grade in accordance with the methods and systems described herein. The wound classification scale (wound grade) exemplified herein facilitates eliminating the subjectivity of the observer/clinician which is inherent is all conventional wound classification schemes. In addition to the wound classification scale, suggested treatment options based on the classification may be provided to the clinician (e.g., wound classification scale number/letter; etiology DFU (confidence 80%) and arterial ulcer (confidence 65%); suggested treatments HBOT (40 dives—2/week), Dermacell® (80%), Amputation (50%), do nothing (10%)).

The examples demonstrate a set of unique advantages that can be practically achieved by utilizing machine learning algorithms in application to the blood flow and/or perfusion analysis of tissue (e.g., wound tissue). In some embodiments, the input data to the algorithms is not dependent on preprocessing or detailed understanding of the blood flow dynamics. As a result, the accuracy of the analysis depends primarily on the quality of the measured signals rather than on a subjective human selection of relevant parameters. Furthermore, the machine learning classification and characterisation results are much less susceptible to noise in the input signal due to the advantages of 'big data' processing. Furthermore, the spatial map generated according to the methods and systems described herein based on machine learning demonstrates both simplicity of interpretation and overall accuracy of the results. It can be used as a viable replacement for and/or a complement to the currently implemented and yet-to-be-conceptualized visual maps and/or images. Since the color scheme of the spatial map can be easily associated with the centroids representing different angiographic curve classes, there is no need for manual region of interest (ROI) selection and subsequent graph generation. By just looking at the spatial map and its corresponding color legend of centroids, the user can immediately assess the blood flow patterns throughout the entire image area. Furthermore, as described in connection with the methods and systems, once the clustering model has been trained on a relevant dataset, it can be stored on any computational platform. The model is highly scalable and can be easily expanded to other modalities (i.e., plastic, MIS, pressure ulcers, etc.).

Example embodiments, and optional variations thereof, have been disclosed herein, and although specific terms are employed, they are used and are to be interpreted in a generic and descriptive sense only and not for purpose of limitation. In some instances, as would be apparent to one of ordinary skill in the art as of the filing of the present application, features, characteristics, and/or elements described in connection with a particular embodiment may be used singly or in combination with features, characteristics, and/or elements described in connection with other embodiments unless otherwise specifically indicated. Accordingly, it will be understood by those of skill in the art that various changes in form and details may be made without departing from the spirit and scope of the present invention as set forth in the following.

While the present disclosure has been illustrated and described in connection with various embodiments shown and described in detail, it is not intended to be limited to the details shown, since various modifications and structural changes may be made without departing in any way from the scope of the present disclosure. Various modifications of form, arrangement of components, steps, details and order of operations of the embodiments illustrated, as well as other embodiments of the disclosure may be made without departing in any way from the scope of the present disclosure, and will be apparent to a person of skill in the art upon reference to this description. It is therefore contemplated that the appended claims will cover such modifications and embodiments as they fall within the true scope of the disclosure. For the purpose of clarity and a concise description, features are described herein as part of the same or separate embodiments; however, it will be appreciated that the scope of the disclosure includes embodiments having combinations of all or some of the features described. For the terms "for example" and "such as," and grammatical equivalences thereof, the phrase "and without limitation" is understood to follow unless explicitly stated otherwise. As used herein, the singular forms "a", "an", and "the" include plural referents unless the context clearly dictates otherwise.

What is claimed is:

1. A method for characterizing tissue of a subject, the method comprising,
   at a computer system having one or more processors and a display:
      receiving data for a time series of fluorescence images of the tissue of the subject, the time series of fluorescence images being or having been captured by an image capture system;
      identifying one or more attributes of the data that are relevant to a clinical characterization of the tissue;
      determining a number of clusters for categorization of the data into a plurality of clusters, wherein determining the number of clusters comprises comparing performance of a plurality of clusterings, wherein comparing performance of the plurality of clusterings comprises assessing respective distortions for the plurality of clusterings;
      categorizing the data into the determined number of clusters based on the one or more attributes of the data such that data in the same cluster are more similar to each other than the data are to data in other clusters, wherein the clusters characterize the tissue;
      generating a spatial map representing clinical characterization of the tissue, wherein the spatial map comprises a plurality of spatial values associated with spatial regions of the tissue and each spatial value is generated based on a cluster of the plurality of clusters; and
      displaying an image based on the spatial map.

2. The method of claim 1, wherein the data for the plurality of time series of fluorescence images of the subject comprises raw data, pre-processed data, or a combination thereof.

3. The method of claim 2, wherein the pre-processed data is pre-processed by applying data compression, principal component analysis, autoencoding, or a combination thereof.

4. The method of claim 1, wherein the one or more attributes of the data relevant to the clinical characterization of the tissue are identified for a plurality of subregions in the time series of fluorescence images of the subject.

5. The method of claim 4, wherein at least one of the subregions is a pixel or a voxel in the time series of fluorescence images.

6. The method of claim 4, wherein at least one of the subregions is a group of pixels or a group of voxels in the time series of fluorescence images of the subject.

7. The method of claim 1, wherein the one or more attributes of the data for the time series of fluorescence images of the subject comprise a time-intensity curve, a coefficient, spatial position, onset time, time to blush, maximum fluorescence intensity, ingress of blood, egress of blood, or a combination thereof.

8. The method of claim 1, wherein the clusters characterize the tissue based on spatial distribution of the clusters, properties of the clusters, cluster data, or a combination thereof.

9. The method of claim 8, wherein properties of the clusters comprise shape of the clusters.

10. The method of claim 1, wherein each cluster is represented by a centroid.

11. The method of claim 10, wherein a centroid of a cluster is indicative of which of the one or more attributes of the data for the time series of fluorescence images of the subject contributes to data categorization.

12. The method of claim 1, wherein categorizing the data for the time series of fluorescence images of the subject into the plurality of clusters comprises categorizing the data into ten or fewer clusters.

13. The method of claim 1, wherein categorizing the data for the time series of fluorescence images of the subject comprises applying an unsupervised clustering algorithm.

14. The method of claim 13, wherein the clustering algorithm is a K-means algorithm.

15. The method of claim 1, wherein the spatial map represents differences in blood flow, perfusion patterns, or a combination thereof among the spatial regions of the tissue.

16. The method of claim 1, further comprising training a machine learning model based on the categorized data.

17. The method of claim 16, wherein the machine learning model is trained in a supervised machine learning algorithm.

18. The method of claim 1, further comprising:
   receiving data for a subject time series of fluorescence images of the tissue of the subject;
   associating a respective cluster of the plurality of clusters with each of a plurality of subregions in the subject time series of fluorescence images;
   generating a subject spatial map based on the associated clusters for the plurality of subregions in the subject time series of fluorescence images; and
   displaying the subject spatial map.

19. The method of claim 18, wherein generating the subject spatial map comprises assigning at least one of an intensity value and a color to each subregion in the subject time series of fluorescence images based on the associated cluster.

20. The method of claim 1, wherein comparing performance of the plurality of clusterings comprises calculating a cumulative distortion for the plurality of clusterings.

21. A system comprising:
a display;
one or more processors;
memory; and
one or more programs, wherein the one or more programs are stored in the memory and configured to be executed by the one or more processors, the one or more programs including instructions for:
receiving data for a time series of fluorescence images of the tissue of the subject, the time series of fluorescence images being or having been captured by an image capture system;
identifying one or more attributes of the data that are relevant to a clinical characterization of the tissue;
determining a number of clusters for categorization of the data into a plurality of clusters, wherein determining the number of clusters comprises comparing performance of a plurality of clusterings, wherein comparing performance of the plurality of clusterings comprises assessing respective distortions for the plurality of clusterings;
categorizing the data into the determined number of clusters based on the one or more attributes of the data such that data in the same cluster are more similar to each other than the data are to data in other clusters, wherein the clusters characterize the tissue;
generating a spatial map representing clinical characterization of the tissue, wherein the spatial map comprises a plurality of spatial values associated with spatial regions of the tissue and each spatial value is generated based on a cluster of the plurality of clusters; and
displaying an image based on the spatial map.

22. The system of claim 21, wherein the one or more programs include instructions for superimposing the image on an anatomical image of the tissue.

23. The system of claim 21, further comprising a light source that provides an excitation light to induce fluorescence emission from a fluorescence imaging agent in the tissue.

24. The system of claim 23, further comprising an image acquisition assembly configured to generate the time series of fluorescence images based on the fluorescence emission.

25. A non-transitory computer-readable storage medium storing one or more programs for execution by a computing system with one or more processors and a display, the one or more programs comprising instructions for:
receiving data for a time series of fluorescence images of the tissue of the subject, the time series of fluorescence images being or having been captured by an image capture system;
identifying one or more attributes of the data that are relevant to a clinical characterization of the tissue;
determining a number of clusters for categorization of the data into a plurality of clusters, wherein determining the number of clusters comprises comparing performance of a plurality of clusterings, wherein comparing performance of the plurality of clusterings comprises assessing respective distortions for the plurality of clusterings;
categorizing the data into the determined number of clusters based on the one or more attributes of the data such that data in the same cluster are more similar to each other than the data are to data in other clusters, wherein the clusters characterize the tissue;
generating a spatial map representing clinical characterization of the tissue, wherein the spatial map comprises a plurality of spatial values associated with spatial regions of the tissue and each spatial value is generated based on a cluster of the plurality of clusters; and
displaying an image based on the spatial map.

26. A method for characterizing tissue of a subject, the method comprising:
receiving data for a subject time series of fluorescence images of the subject, the subject time series of fluorescence images of the subject being or having been acquired by an image acquisition device;
determining a number of subregions for association of the data with a plurality of subregions, wherein determining the number of subregions comprises comparing performance of a plurality of clusterings, wherein comparing performance of the plurality of clusterings comprises assessing respective distortions for the plurality of clusterings;
associating a respective category of a predetermined plurality of categories with each of the determined number of subregions in the subject time series of fluorescence images, wherein the categories characterize tissue and are based on one or more attributes relevant to a clinical characterization of tissue, such that a subregion associated with a given category is more similar to other subregions associated with the given category than subregions associated with other categories;
generating a spatial map representing the tissue based on the associated categories for the plurality of subregions in the subject time series of fluorescence images; and
displaying the spatial map as an image.

* * * * *